United States Patent [19]

Ely et al.

[11] Patent Number: 5,424,409

[45] Date of Patent: Jun. 13, 1995

[54] **DNA CONSTRUCTS ENCODING *BACILLUS THURINGIENSIS* TOXINS FROM STRAIN A20**

[75] Inventors: Susan Ely, Bucks; Janet M. Tippett, Reading, both of England

[73] Assignee: Imperial Chemical Industries PLC, London, England

[21] Appl. No.: 671,817

[22] PCT Filed: Sep. 29, 1989

[86] PCT No.: PCT/GB89/01157

§ 371 Date: Apr. 1, 1991

§ 102(e) Date: Apr. 1, 1991

[87] PCT Pub. No.: WO90/03434

PCT Pub. Date: Apr. 5, 1990

[30] Foreign Application Priority Data

Sep. 30, 1988 [GB] United Kingdom ............... 8823068

[51] Int. Cl.⁶ .................... C12N 15/00; C07H 17/00; A01N 63/00
[52] U.S. Cl. ........................ 536/23.71; 424/93.461; 536/23.4
[58] Field of Search ............ 424/93 L; 536/27, 23.71, 536/23.4; 935/47, 10

[56] References Cited

U.S. PATENT DOCUMENTS 5,061,489  10/1991  Bernier et al. .................. 424/93

FOREIGN PATENT DOCUMENTS 228838  7/1987  European Pat. Off. .
269601  6/1988  European Pat. Off. .

OTHER PUBLICATIONS

Chemical Abstracts, vol. 108, No. 21, 23 May 1988. (Columbus, Ohio, US), Hefford, Mary Alice et al: "Sequence of a lepidopteran toxin gene of *Bacillus thuringiensis* subsp kurstaki NRD-12.", see p. 182, abstract 181175c, & J. Biotechnol. 1987, 6(4), 307–22.

Hofte et al., *Appl. Env. Microb.*, vol. 54, No. 8, Aug. 1988, pp. 2010–2017.

Prefontaine et al., *Appl. Env. Microb*, vol. 53, No. 12, Dec. 1987, pp. 2808–2814.

Hefford et al., *J. Biotech.*, vol. 6, pp. 307–322, 1987.

*Primary Examiner*—Robert A. Wax
*Assistant Examiner*—Keith D. Hendricks
*Attorney, Agent, or Firm*—Cushman, Darby & Cushman

[57] ABSTRACT

Recombinant DNA coding for an insecticidally active form of the *Bacillus thuringiensis* endotoxin which DNA is derived from the chromosome plasmids of the A20 strain of *Bacillus thuringiensis*. The recombinant genes may be of the 6.6, 5.3 or 4.5 types. Further discloses a truncated chimetic endotoxin-producing gene derived from the 5.3 and 4.5-type genes of strain A20.

7 Claims, 54 Drawing Sheets

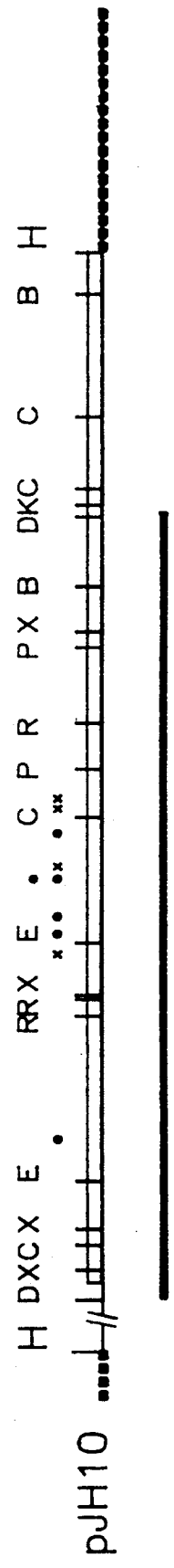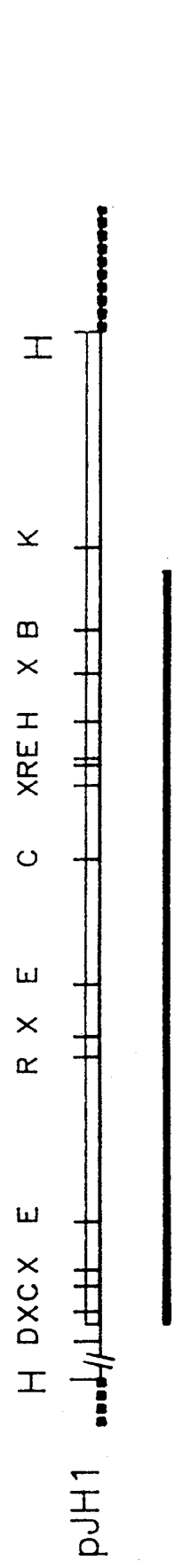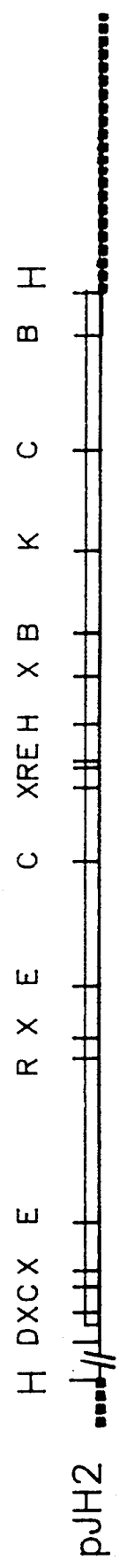
FIG. IA  FIG. IB  FIG. IC

FIG. 3A1

MAPSEQ V5.10 PIC33INS.SEQ(1,2990) Reading frames: 3    Enzyme file ALL.ENZ

```
                                                            M     M
                          M       M                         S     A
                          S       N                         E     E
                          E       L                         1     3
                          1       1
TATGTTTTAAATTGTAGTAATGAAAAACAGTATTATATCATAATGAATTGGTATCTTAATAAAGAGATGGAGGTAACTTATGGATAACAATCCGAACAT
---+----+----+----+----+----+----+----+----+----+----+----+----+----+----+----+----+----+----+----+    100
ATACAAAATTTAACATCATTACTTTTTGTCATAATATAGTATTACTTAACCATAGAATTATTTTCTCTACCTCCATTGAATACCTATTGTTAGGCTTGTA c  f  k  l  .  .  k  t  v  l  y  h  n  e  l  v  s  .  .  k  r  w  r  .  l  m  d  n  n  p  n  i

XBBNA                 M    M                                            M  B               C T
   MSSSV                 S    A                                            A  S               L A
   NMMIA                 E    E                                            E  R               A Q
   11113                 1    3                                            3  1               1 1
   / / /                                                                   /
CAATGAATGCATTCCTTATAATTGTTTAAGTAACCCTGAAGTAGAAGTATTAGGTGGAGAAAGAATAGAAACTGGTTACACCCCAATCGATATTTCCTTG
---+----+----+----+----+----+----+----+----+----+----+----+----+----+----+----+----+----+----+----+    200
GTTACTTACGTAAGGAATATTAACAAATTCATTGGGACTTCATCTTCATAATCCACCTCTTTCTTATCTTTGACCAATGTGGGGTTAGCTATAAAGGAAC n  e  c  i  p  y  n  c  l  s  n  p  e  v  e  v  l  g  g  e  r  i  e  t  g  y  t  p  i  d  i  s  l
```

FIG. 3A2

```
                    XT   NSH                          SM                        AANF
                    MT   CCP                          PA                        VSLI
                    NH   IRA                          EE                        AUAN
                    12   112                          11                        2141
                     /   //                                                     //
TCGCTAACGCAATTTCTTTTGAGTGAATTGTTCCCGGTGCTGGATTTGTGTTAGGACTAGTTGATATAATATGGGGAATTTTTGGTCCCCTCTCAATGGG   300
---+----+----+----+----+----+----+----+----+----+----+----+----+----+----+----+----+----+----+----+
AGCGATTGCGTTAAAGAAGAAAACTCACTTAAACAGGGCCACGACCTAAACACAATCCTGATCAACTATATTATACCCCTTAAAAACCAGGAGAGTTACCC
 s  l  t  q  f  l  l  s  e  f  v  p  g  a  g  f  v  l  g  l  v  d  i  i  w  g  f  f  g  p  s  q  w  d

F   H  R                   M  M                E        HM M  N              XM       D
  I   G  S                   S  S                C        NA B  L              BA       D
  N   A  A                   E  E                R        FE O  A              AE       E
  1   1  1                   1  1                1        31 2  4              11       1

ACGCATTTCTTGTACAAATTGTAATTAACAGTTAATTAACCAAAGAATAGAAGAATTCGCTAGGAACCAAGCCATTTCTAGATTAGAAGGACTAAGCAATCTTTA   400
---+----+----+----+----+----+----+----+----+----+----+----+----+----+----+----+----+----+----+----+
TGCGTAAAGAACATGTTTAACTTGTTAATTAGTCAATTAATTGGTTTCTTATCTTCTTAAGCGATCCTTGGTTCGGTAAGATCTAATCTTCCTGATTCGTTAGAAAT
 a  f  l  v  q  i  e  q  l  l  n  q  r  i  e  e  f  a  r  n  q  a  i  s  r  l  e  g  l  s  n  l  y
```

FIG. 3A3

```
         H                    XMD B              MS KE   T    M           N
         N                    HBP I              SF SA   T    B           L      N S
         F                    OON N              EA PR   H    O           A      P 2
         1                    211 1              1N 21   2    2           3             500
TCAAATTTACGCAGAATCTTTTAGAGAGTGGGAAGCAGAGATCCTACTAATCCAGCATTAAGAAGAGATGGCGTATTCAATTCAATGACATGAACAGTGCC
---+----+----+----+----+----+----+----+----+----+----+----+----+----+----+----+----+----+----+----+
AGTTTAAATGGCGTCTTAGAAAATCTCTCACCCTTCGTCTCTAGGATGATTAGGTCGTAATTCTTCTCTACGCATAAGTTAAGTTACTGTACTTGTCACGG q  i  y  a  e  s  f  r  e  w  e  a  d  p  t  n  p  a  l  r  e  e  m  r  i  q  f  n  d  m  n  s  a
---+----+----+----+----+----+----+----+----+----+----+----+----+----+----+----+----+----+----+----+
```

FIG. 3BI

```
MAPSEQ V5.10 PIC33INS.SEQ(1,2990) Reading frames: 3   Enzyme file ALL.ENZ

M                        M B          A F
                                                   N                        N B          L N
                                                   L                        L V          U U
                                                   1                        1 1          1 H
CTTACAACCGCTATTCCTCTCTTTTGGCAGTTCAAAATTATCAAGTTCCTCTCTTTTATCAGTATGTTCAAGCTGCAAATTACATTTATCAGTTTTGAGAG
----+----|----+----|----+----|----+----|----+----|----+----|----+----|----+----|----+----|----+----   600
GAATGTTGGCGATAAGGAGAGAAACCGTCAAGTTGTTTTAATAGTTCAAGGAGAGAAAATAGTCATATACAAGTTCGACGTTTAAATGTAAATAGTCAAAACTCTC l  t  t  a  i  p  l  l  a  v  q  n  y  q  v  p  l  l  s  v  y  v  q  a  a  n  l  h  l  s  v  l  r  d

S                        F T                                         M  M
                  F                        N H                                         S  A
                  A                        U A                                         E  E
                  N                        H 1                                         1  1
ATGTTTCAGTGTTTGGACAAAGGTGGGGATTTGATGCCGCGACTATCAATAGTCGTTATATAATGATTTAACTAGGCTTATTGGCAACTATACAGATTATGC
----+----|----+----|----+----|----+----|----+----|----+----|----+----|----+----|----+----|----+----   700
TACAAAGTCACAAACCTGTTTCCACCCCTAAACTACGGCGCTGATAGTTATCAGCAATATTACTAAATTGATCCGAATAACCGTTGATATGTCTAATACG v  s  v  f  g  q  r  w  g  f  d  a  a  t  i  n  s  r  y  n  d  l  t  r  l  i  g  n  y  t  d  y  a
```

FIG. 3B2

```
              MA           ANAFH H  XM                 KE     MM
              AF           VLSIP N  BA                 SA     SB
              EL           AAUNA F  AE                 PR     EO
              23           24112 1  11                 21     12
 RR                         /       /                   /      /
 SS
 AA
 11
TGTACGCTGGTACAATACGGGATTAGAACGTGTATGGGGACCGGATTCTAGAGATTGGGTAAGGTATAATCAATTTAGAAGAGAATTAACACTAACTGTA
---:--+----:----+----:----+----:----+----:----+----:----+----:----+----:----+----:----+----:----+  800
---:--+----:----+----:----+----:----+----:----+----:----+----:----+----:----+----:----+----:----+
ACATGCGACCATGTTATGCCCTAATCTTGCACATACCCCTGGCCTAAGATCTCTAACCCATTCCATATTAGTTAAATCTTCTCTTAATTGTGATTGACAT v  r  w  y  n  t  g  l  e  r  v  w  g  p  d  s  r  d  w  v  r  y  n  q  f  r  r  e  l  t  t  v

H                    E   MATH    X  M
                  N                    C   BSAN    M  S
                  F                    R   OUQF    N  E
                  3                    V   2213    1  1
                  /                    /    /       /  /
TTAGATATCGTTGCTCTGTTCCCGAATTATTGATAGTAGAAGATATCCAATTCGAACAGTTTCCCAATTAACAAGAGAAATTTATACAAACCCAGTATTAG
---:--+----:----+----:----+----:----+----:----+----:----+----:----+----:----+----:----+----:----+  900
---:--+----:----+----:----+----:----+----:----+----:----+----:----+----:----+----:----+----:----+
AATCTATAGCAACGAGACAAGGGCTTAATACTATCATCTTCTATAGGTTAAGCTTGTCAAAGGGTTAATTGTTCTCTTTAAATATGTTTGGGTCATAATC l  d  i  v  a  l  f  p  n  y  d  s  r  r  y  p  i  r  t  v  s  q  l  t  r  e  i  y  t  n  p  v  l  e
```

FIG. 3B3

```
          M  T    D                              H  P          M        S  S
          N  A    D                              N  L          S        P  F
          L  Q    E                              F  E          E        O  A
          1  1    1                              1  1          1        1  N
                                                                        1                    1000
AAAATTTGATGGTAGTTTTCGAGGCTCGGGCATAGAAAGAAGTATTAGGAGTCCACATTTGATGGATATACTTAACAGTATAACCATCTATAC
---:-+----:----+----:----+----:----+----:----+----:----+----:----+----:----+----:----+----:-
TTTTAAACTACCATCAAAGCTCCGAGCCGAGTCCCGTATCTTTCTTCATAATCCTCAGGTGTAAACTACCTATATGAATTGTCATATTGGTAGATATG n f d g s f r g s a g g i e r s i r s p h l m d i l n s i t i y t
```

FIG. 4AI

MAPSEQ V5.10 PIC33INS.SEQ(1,2990) Reading frames: 3   Enzyme file ALL.ENZ

```
                        F             S         A N H          E     M       N SNS
                        O             F         S L A          C     A       L TCE
                        K             A         U A E          R     E       A YOC
                        1             N         1 4 3          1     2       4 111
                                                                                 //
GGATGCTCATAGGGGTTATTATTATTGGTCAGGGCATCAAATAATGGCTTCTCCTGTCGGGTTTTCGGGGCCAGAATTCACGTTTCCGCTATATGGAACC  1100
---+---------+---------+---------+---------+---------+---------+---------+---------+---------+---
---+---------+---------+---------+---------+---------+---------+---------+---------+---------+---
CCTACGAGTATCCCCAATAATAACCAGTCCCGTAGTTTATTACCGAAGAGGACAGCCCAAAAGCCCGGTCTTAAGTGCAAAGGCGATATACCTTGG d  a  h  r  g  y  y  y  w  s  g  h  q  i  m  a  s  p  v  g  f  s  g  p  e  f  t  f  p  l  y  g  t

N             F  A           B M                                   M        M B     E  M  M
 L             N  L            B A                                  A        N B     C  S  B
 A             U  U            V E                                  E        L V     P  E  O
 3             H  1            1 2                                  1        1 2     1  1  2
ATGGGAAAATGCAGCTCCACAACAACGTATTGTTGCTCAACTAGGTCAGGGCGTGTATAGAACATTATCCTCACTTTTTATAGAAGACCTTTTAATATAG  1200
---+---------+---------+---------+---------+---------+---------+---------+---------+---------+----
---+---------+---------+---------+---------+---------+---------+---------+---------+---------+----
TACCCTTTACGTCGAGGTGTTGTTGCATAACAACGAGTTGATCCAGTCCCGCACATATCTTGTAATAGGAGATGAAAATATCTTCTGGAAAATTATATC m  g  n  a  a  p  q  q  r  i  v  a  q  l  g  q  g  v  y  r  t  l  s  s  t  f  y  r  r  p  f  n  i  g
```

FIG. 4A2

```
                    F        N F      M M    N S A
                    I        L O      N N    S N C
                    N        A K      L L    P A C
                    1        4 1      1 1    B 1 1
GGATAAATAATCAACAACTATCTGTTCTTGACGGGACAGAATTTGCTTATGGAACCTCCTCAAATTTGCCATCCGCTGTATACAGAAAAAGCGGAACGGT
---:-:-+----:+----+---------+--------:-+----+---------+---------+--------:+----+---------+---------+    1300
CCTATTTATTAGTTGTTGATAGACAAGAACTGCCCTGTCTTAAACGAATACCTTGGAGGAGTTTAAACGGTAGGGACATATGTCTTTTCGCCTTGCCA i n n q q l s v l d g t e f a y g t s s n l p s a v y r k s g t v

F              M            CT M      N
              O              A            LA S      L
              K              E            AQ E      A
              1              2            11 1      3

H              SABSEM
              N              TVGECA
              F              YRLCOE
              3              121111
                             / /  /
AGATTCGCTGGATGAAATACCACCACAGAATAACAACGTGCCACCTAGGCAAGGATTTAGTCATCGATTAAGCCATGTTTCATGTTTCGTTCAGGCTCT
---:-----+---:----+---------+---------+-----:---+----:----+---------+---------+---------+---------+    1400
TCTAAGGCGACCTACTTTATGGTGGTGTCTTATTGTTGCACGGTGGATCCGTTCCTAAATCAGTAGCTAATTCGGTACAAGCTAATTCGGTACAAAGCAAGTCCGAGA d s l d e i p p q n n n v p p r q g f s h r l s h v s m f r s g s
```

FIG. 4A3

```
A SHBN                                                                              M                              S
L SGAS                                                                              S                              F
U TINP                                                                              E                              A
1 1A22                                                                              1                              N
  ///
AGTAGTAGTGTAAGTATATAATAAGAGCTCCTATGTTCTCTTGGATACATCGTAGTGCTGAATTTAATAATATAATTGCATCGGATAGTATTACTCAAATCC
----+----:----+----:----+----:----+----:----+----:----+----:----+----:----+----:----+----:----+----:   1500
TCATCATCACATTCATATATTATTCTCGAGGATACAAGAGAACCTATGTAGCATCACGACTTAAATTATTATATTAACGTAGCCTATCATAATGAGTTTAGG s  s  s  v  s  s  i  i  r  a  p  m  f  s  w  i  h  r  s  a  e  f  n  n  i  i  a  s  d  s  i  t  q  i  p
----+----:----+----:----+----:----+----:----+----:----+----:----+----:----+----:----+----:----+----:
```

FIG. 4BI

MAPSEQ V5.10 PIC33INS.SEQ(1,2990) Reading frames: 3    Enzyme file ALL.ENZ

```
P                           M                              AAE AS        FD        M
S                           S                              VSC PC        ID        S
T                           E                              AUR,YR        NE        E
1                           1                              212 11        11        1
                                                              /           /
CTGCAGTGAAGGGAAACTTTCTTTTTAATGGTTCTGTAATTTCAGGACCAGGATTTACTGGTGGGGGACTTAGTGTAGATTAAATAGTAGTGGAAATAACAT
---.---+---.---+---.---+---.---+---.---+---.---+---.---+---.---+---.---+---.---+---.---+---.---+---.  1600
GACGTCACTTCCCTTTGAAAGAAAAATTACCAAGAGACATTAAAGTCCTGGTCCTAAATGACCACCCTGAATCAATCTAATTTATCATCACCTTTATTGTA a   v   k   g   n   f   l   f   n   g   s   v   i   s   g   p   g   f   t   g   g   d   l   v   r   l   n   s   s   g   n   n   i
---.---+---.---+---.---+---.---+---.---+---.---+---.---+---.---+---.---+---.---+---.---+---.---+---.

E  T                      R                      M  H  H
                                    C  A                      S                      A  P  N
                                    A  Q                      A                      E  H  F
                                    V  1                      1                      3  1  1

TCAGAATAGAGAGGGTATATTGAAGTTCCAATTCACTTCCCATGCACTATCCAGATATCGAGTTCGTGTACGGTATGCTTCTGTAACCCGATTCACCTC
---.---+---.---+---.---+---.---+---.---+---.---+---.---+---.---+---.---+---.---+---.---+---.---+---.  1700
AGTCTTATCTCCCATATAACTTCAAGGTTAAGTGAAGGGTAGCTGTAGATGGTCTATAGCTCAAGCACATGCCATACGAAGACATTGGGGCTAAGTGGAG

```
M   MFM
A   SON                                             R  A  AM
E   EKL                                             S  L  LA
2   111                                             A  U  UE
                                                    1  1  12

AACGTTAATTGGGGTAATTCATCCATTTTTTCCAATACAGTACCAGCTACGTCATTAGATAATCTACAGTGATTTTGGTTATTTTGAAA     1800
----+----+----+----+----+----+----+----+----+----+----+----+----+----+----+----+----+----+
TTGCAATTAACCCCATTAAGTAGGTAAAAAAGGTTATGTCATGGTCGATGTCAGTAATCTCATTAGATGTTAGTTCACTAAAACCAATAAAACTTT n  v  n  w  g  n  s  s  i  f  s  n  t  v  p  a  t  a  t  s  l  d  n  l  q  s  s  d  f  g  y  f  e  s

F  P                                                X  BM
                       I  S                                                M  SA
       M               N  T                                                N  RE
       B               1  1                                                1  13
       O
       2

GTGCCAATGCTTTACATCTTCATTAGGTAATATAGTAGGTGTTAGAAATTTAGTGGGACTGCAGGAGTGATAATAGACAGATTTGAATTTATTCCAGT     1900
----+----+----+----+----+----+----+----+----+----+----+----+----+----+----+----+----+----+
CACGGTTACGAAATGTAGAAGTAATCCATTATATCATCCACAATCTTTAAAATCACCCTGACGTCCTCACTATTATCTGTCTAAACTTAAATAAGGTCA a  n  a  f  t  s  s  l  g  n  i  v  g  v  r  n  f  s  g  t  a  g  v  i  i  d  r  f  e  f  i  p  v
```

FIG. 4B3

```
A       H H                         H BH H  M A                 M
M       XAT        H I              I SH P  A C                 A
L  N L  HVA        N A              N MA H  E C                 E
W  L 1  OAQ        P 1              P 11 1  2 1                 1
N       111        /                         /                  3
   TACTGCAACACTCGAGGCTGAATATAATCTGGAAAGAGGCGCAGAAGGGCTGAATGCGCTGTTTACGTCTACAAACCAACTAGGCTAAAAACAAATGTA
   ---+----+----

FIG. 5AI

MAPSEQ V5.10 PIC33INS.SEQ(1,2990) Reading frames: 3   Enzyme file ALL.ENZ

```
          M  MS                          F                   NN
          A  AN                          O                   SL
          E  EA                          K                   PA
BMD       3  2B                          1                   H3
CBP                                                                      2100
LON
111
ACGGATTATCATATTGATCAAGTGTCCAATTTAGTTACGTATTTATCGGATGAATTTTGTCTGATGAAAAGCGAGAATTGTCCAGAAAGTCAAACATG
-----+---------+---------+---------+---------+---------+---------+---------+---------+---------+
TGCCTAATAGTATAACTAGTTCACAGGTTAAATCAATGCATAAATAGCCTACTTTTCGCTCTTAACAGGTCTCTTTCAGTTTGTAC t d y h i d q v s n l v t y l s d e f c l d e k r e l s e k v k h a

S                       H             AM             MP              F R
P    P                       N             SS             AF              O S
L    O                       F             EE             EI              K A
E    1                       1             11             21              1 1
N
F
1
CGAAGCGACTCAGTGATGATGAACGCAATTTACTCCAAGATTCAAATTTCAAAGACATTAATAGGCAACCAGAACGTGGGTGGGGCGGAAGTACAGGGATTAC
-----+---------+---------+---------+---------+---------+---------+---------+---------+---------+
GCTTCGCTGAGTCACTACTACTTGCGTTAAATGAGGTTCTAAGTTTAAAGTTTCTGTAATTATCCGTTGGTCTTGCACCCACCCCGCCTTCATGTCCCTAATG 2200 k r l s d e r n l l q d s n f k d i n r q p e r g w g g s t g i t
```

FIG. 5A2

```
         M           M              MM                        T   CT   H
     M   SS    MDF   A              AA                        T   LA   N
     N   TE    SRO   E      BANRK   EE                        H   AQ   F
     L   YC    EAK   2      ASLSP   23                        2   11   1
     1   11    111          NPAAN                                          
                            11411

CATCCAAGGAGGGGATGACGTATTTAAAGAAAAATTACGTCACACTATCAGGTACCTTTGATGAGTGCTATCCAACATATTTGTATCAAAAAATCGATGAA  2300
-----+---------+---------+---------+---------+---------+---------+---------+---------+---------+
GTAGGTTCCTCCCCTACTGCATAAATTTCTTTTAATGCAGTGTGATAGTCCATGAAACTACTCACGATAGTTGTATAAACATAGTTTTTTAGCTACTT i  q  g  g  d  d  v  f  k  e  n  y  v  t  l  s  g  t  f  d  e  c  y  p  t  y  l  y  q  k  i  d  e

M                                T              MD                       M    H        N
             M                                A              BD                       S    N        L
             S                                Q              OE                       E    F        A
             E                                1              21                       1    3        3
             1

TCAAAAATTAAAAAGCCTTTACCCGTTATCAATTAAGAGGGTATATCGAAGATAGTCAAGACTTAGAAAATCTATTTAATTCGCTACAATGCAAAACATGAAA  2400
-----+---------+---------+---------+---------+---------+---------+---------+---------+---------+
AGTTTTTAATTTTCGGAAATGGGCAATAGTTAATTCTCCCATATAGCTTCTATCAGTTCTGAATCTTTAGATAAATTAAGCGATGTTACGTTTTGTACTTT s  k  l  k  a  f  t  r  y  q  l  r  g  y  i  e  d  s  q  d  l  e  i  y  l  i  r  y  n  a  k  h  e  t
```

FIG. 5A3

```
     E  AS   R   N               GCHF       S  HH  CT  HBHTHH
     C  PC   S   L               DFAN       F  NN  LA  ISHHHI
     R  YR   A   A               IREU       A  FF  AQ  NSAAAN
     2  11   1   4               213H       N  31  11  P2111P

CAGTAAATGTGCCAGGTACGGGTTCCTTATGGCCGCTTTCAGCCCAAAGTCCAATCGGAAAGTGTGGAGAGCCGAATCGATGCGCCACACCTTGAATG  2500
----+----+----+----+----+----+----+----+----+----+----+----+----+----+----+----+----+----+----+----
GTCATTTACACGGTCCATGCCCAAGGAATACCGGCGAAAGTCGGGTTTCAGGTTAGCCTTTCACACCTCTCGGCTTAGCTACGCGGTGTGGAACTTAC v  n  v  p  g  t  g  s  l  w  p  l  s  a  q  s  p  i  g  k  c  g  e  p  n  r  c  a  p  h  l  e  w
```

```
                        B     M
                        S     A
                        M     E
                        2     2
HEHHNMA
ICHAHAL
N4AEEEU
P712111
          AAGGCGTAGCTCGTGTGAAAAGAGAGCGGAGAAAAATTGGAGAGACAAACGTGAAAAATTGGGAAACAATATCGTTTATAAAGAGGCAAAAGAATC    2800
          ----+----:----+----:----+----:----+----:----+----:----+----:----+----:----+----:----+----:----+----:
          TTCGCGATCGAGCACACACTTTTCTCGCCTCTCTGTTTTTAACCTCTCTGTTGCACTTTTTAACCCTTACCCTTTGTTTATAGCAAATATTTCTCCGTTTTCTTAG
                                                                                                        SH
                                                                                                        FN
                                                                                                        AF
                                                                                              M         N1
                                                                                              N
                                                                                              L
                                                                                              1 a   l   a   r   v   k   r   a   e   k   k   w   r   d   k   r   e   k   l   e   w   e   t   n   i   v   y   k   e   a   k   e   s

BMD                          H     S              NHE      NF                 MA                             B     T H
          CBP                          N     S              LNC      LN                 AF                             S     A N
          LON                          F     P              AFD      AU                 EL                             M     Q F
          111                          3     1              31X      3H                 23                             1     1 3
          TGTAGATGCTTTATTTGTAAACTCTCAATATGATCAATTACAAGCGGATACGAATATTGCCATGATTCATGGGCAGATAAACGTGTTCATAGCATTCGA           2900
          ----+----:----+----:----+----:----+----:----+----:----+----:----+----:----+----:----+----:----+----:
          ACATCTACGAAATAAACATTTGAGAGTTATACTAGTTAATGTTCGCCTATGCTTATAACGGTACTAAGTATCGCACAAGTATCGTAAGCT v   d   a   l   f   v   n   s   q   y   d   q   l   q   a   d   t   n   i   a   m   i   h   a   a   d   k   r   v   h   s   i   r
```

FIG. 5B3

```
         H        N    A                                                                          H
         I        L    L                                                                          P
         N        A    U                                                                          A
         3        3    1                                                                          2
GAAGCTTGGGCGTAATCATGGTCATAGCTGTTTCCTGTGTGAAATTGTTATCCGCTCACAATTCCACACAACATACGAGCCGGAAGCATAA
---+---+---+---+---+---+---.---+---+---+---.---+---+---+---+---+---+---+---+---+---+---+ 2990
CTTCGAACCGCATTAGTACCAGTATCGACAAAGGACACACTTTAACAATAGGCGAGTGTTAAGGTGTGTTGTATGCTCGGCCTTCGTATT e  a  w  r  n  h  g  h  s  c  f  l  c  e  i  v  i  r  s  q  f  h  t  t  y  e  p  p  e  a  .
---+---+---+---+---+---+---+---+---+---+---+---+---+---+---+---+---+---+---+---+---+---+
```

FIG. 6AI

MAPSEQ V5.10 PIC49INS.SEQ(1,2815) Reading frames: 1 Enzyme file ALL.ENZ

```
                                                                          M
                                        M          M                      A
                                        S          N                      E
                                        E          L                      3
                                        1          1
AAATTGTAGTAATGAAAAACAGTATTATATCATAATGAATTGGTATCTTAATAAAGAGATGGAGGTAACTTATGGATAACAATCCGAACATCAATGAAT
---+----+----+----+----+----+----+----+----+----+----+----+----+----+----+----+----+----+----+----+  100
TTTAACATCATTACTTTTTGTCATAATATAGTATTACTTAACCATAGAATTATTTCTCTACCTCCATTGAATACCTATTGTTAGGCTTGTAGTTACTTA k l . . k t v l y h n e l v s . . k r w r . l m d n n p n i n e c

M B        C T
XBBNA        M M                                            A S        L A
MSSSV        S A                                            E R        A Q
NMMIA        E E                                            3 1        1 1
11113        1 3                                            /          /
GCATTCCTTATAATTGTTAAGTAACCCTGAAGTAGAAGTATTAGGTGGAGAAGAATAGAAACTGGTTACACCCCAATCGATATTTCCTTGTCGCTAAC
---+----+----+----+----+----+----+----+----+----+----+----+----+----+----+----+----+----+----+----+  200
CGTAAGGAATATTAACAAATTCATTGGGACTTCATCTTCATAAGGAAGTATTCCACCTCTTTCTTATCTTTGACCAATGTGGGGTTAGCTATAAAGGAACAGCGATTG i p y n c l s n p e v e v l g g e r i e t g y t p l i d i s l s l t
```

FIG. 6A2

```
                                                              SM                                    AANF            MF
             XT    NSH                                        PA                                    VSLI            NI
             MT    CCP                                        EE                                    AUAN            LN
             NH    IRA                                        11                                    2141            11
             12    112                                                                              //
             //
GCAATTTCTTTTGAGTGAATTTGTTCCGGTGCTGTGGATTTGTGTTAGGACTAGTTGATATAATATGGGAATTTTTGGTCCCTCTCAATGGGACGCATTT   300
---+----|----+----|----+----|----+----|----+----|----+----|----+----|----+----|----+----|----+----|
CGTTAAAGAAAACTCACTTAAACAAGGCCACGACACCTAAACACAATCCTGATCAACTATATTATACCCCTTAAAACCAGGAGAGTTACCCTGCGTAAA q  f  l  l  s  e  f  v  p  g  a  g  f  v  l  g  l  v  d  i  i  w  g  i  f  g  p  s  q  w  d  a  f

M    M                    E    HM M   N               XM        D
             H    R       S    S                    C    NA B   L               BA        D
             G    S       E    E                    R    FE O   A               AE        E
             A    A       1    1                    1    31 2   4               11        1
             1    1
CTTGTACAAATTGAACAGTTAATTAACCAAAGAATAGAAGAATTCGCTAGGAACCAAGCCATTTCTAGATTAGAAGGACTAAGCAATCTTTATCAAATTT   400
---+----|----+----|----+----|----+----|----+----|----+----|----+----|----+----|----+----|----+----|
GAACATGTTTAACTTGTCAATTAATTGGTTTCTTATCTTCTTAAGCGATCCTTGGTTCGGTAAAGATCTAATCTAATTCTGATTCGTTAGAAATAGTTTAAA l  v  q  l  e  q  l  i  n  q  r  i  e  e  f  a  r  n  q  a  i  s  r  l  e  g  l  s  n  l  y  q  i  y
```

FIG. 6A3

```
                              MS  KE   T     M           N
                              SF  SA   T     B           L       N
       XMD   B                EA  PR   H     O           A       S
       HBP   I                IN  21   2     2           3       P
       OON   N                                                   2
       211   1
ACGCAGAATCTTTTAGAGAGTGGGAAGCAGATCCTACTAATCCAGCATTAAGAGAAGAGATGCGTATTCAATTCAATGACATGAACAGTGCCCTTACAAC
----+----:----+----:----+----:----+----:----+----:----+----:----+----:----+----:----+----:----+----  500
TGCGTCTTAGAAAATCTCTCACCCTTCGTCTAGGATGATTAGGTCGTAATTCTCTTCTCTACGCATAAGTTAAGTTACTGTACTTGTCACGGGAATGTTG a  e  s  f  r  e  w  e  a  d  p  t  n  p  a  l  r  e  e  m  r  i  q  f  n  d  m  n  s  a  l  t  t
----+--:-----+--:-----+--:-----+--:-----+--:-----+--:-----+--:-----+--:-----+--:-----+--:-----+--:--
```

```
MAPSEQ V5.10 PIC49INS.SEQ(1,2815) Reading frames: 1  Enzyme file ALL.ENZ

M               M B       A F
                                                    N               N B       L N
                                                    L               L V       U U
                                                    1               1 1       1 H
                                                                                              600
CGCTATTCCTCTCTTTTGCAGTTCAAGTTCCTCTCTTTTGAGAGTTCAAGCTGCAAATTACATTTATCAGTTTGAGAGATGTTCA
---+---------+---------+---------+---------+---------+---------+---------+---------+
GCGATAAGGAGAAAAACGTCAAGTTCAAGGAGAAATAGTCATATACAAGTTCGACGTTTAAATGTAAATAGTCAAACTCTCTACAAGT a  i  p  l  f  a  v  q  n  y  q  v  p  l  l  s  v  y  v  q  a  a  n  l  h  l  s  v  l  r  d  v  s

S                 F T                      M M              M D    N     R
                F                 N H                      S A              B P    L     S
                A                 U A                      E E              O N    A     A
                N                 H 1                      1 1              1 1    3     1
                                                                                              700
GTGTTTGGACAAAGGTGGGGATTTGATGCTGTTGTTTGGACAAAGGTGGGGATTTGATGCTTATTGGCAACTATACAGATCATGCTGTACGCT
---+---------+---------+---------+---------+---------+---------+---------+---------+
CACAAACCTGTTTCCACCCCTAAACTACGACAACAAACCTGTTTCCACCCCTAAATAACCGTTGATATGTCTAGTACGACATGCGA v  f  g  q  r  w  g  f  d  a  a  t  i  n  s  r  y  n  d  l  t  r  l  i  g  n  y  t  d  d  h  a  v  r  w
```

FIG. 6B2

```
                                ANAFH H  XM                KE          M M
                                VLSIP N  BA                SA      M   M B
                                AAUNA F  AE                PR      S   E O
R                               24112 1  11                21      E 1 1 2
S
A
1
GGTACAATACGGGATTAGAGGCGTGTATGGGACCGGATTCTAGAGATTGGATAAGATATAATCAATTAGAAGAGAATTAACACTAACTGTATTAGATAT
---+---------+---------+---------+---------+---------+---------+---------+---------+---------+----  800
CCATGTTATGCCCTAATCTCGCACATACCCCTGGCCTAAGATCTCTAACCTATTCTATATTAGTTAATCTTCTCTTAATTGTGATTGACATAATCTATA y n t g l e r v w g p d s r d w i r y n q f r r e l t l t v l d i

M       ATH X            M
                        A       SAN M            S
                        E       UQF N            E
                        2       213 1            1
CGTTTCTCTATTTCCGAACTATGATAGTAGAACGTATCCAATTCGAACAGTTTCCCAATTAACAAGAGAAATTTATACAAACCCAGTATTAGAAAATTTT
---+---------+---------+---------+---------+---------+---------+---------+---------+---------+----  900
GCAAAGAGATAAAGGCTTGATACTATCATCTTGCATAGGTTAAGCTTGTCAAAGGGTTAATTGTTCTCTTTAAATATGTTTGGGTCATAATCTTTTAAAA v s l f p n y d s r t y p i r t v s q l t r e i y t n p v l e n f
```

FIG. 6B3

```
   M   T   D           H       M       M   S   S       M
   N   A   D           N   P   S       S   P   F       N
   L   Q   E           F   L   E       E   O   A       L
   1   1   1           1   1   1       1   1   N       1
                                                1
GATGGTAGTTTCGAGGCTCGGCTCAGGGCATAGAAGGAAGTATTAGGAGTCCACATTTGATGGATATACTTAACAGTATAACCATCTATACGGATGCTC
----+----|----+----|----+----|----+----|----+----|----+----|----+----|----+----|----+----|----+----|  1000
CTACCATCAAAGCTCCGAGCCGAGTCCCGTATCTTCCTTCATAATCCTCAGGTGTAAACTACCTATATGAATTGTCATATTGGTAGATATGCCTACGAG d   g   s   f   r   g   s   a   q   g   i   e   g   s   i   r   s   p   h   l   m   d   i   l   n   s   i   t   i   y   t   d   a   h
```

FIG. 7AI

MAPSEQ V5.10 PIC49INS.SEQ(1,2815) Reading frames: 1 Enzyme file ALL.ENZ

```
         F           S        A  E
         O           F        N  C
         K           A        H  R
         P           N        1  1
         1                    4
                              3

ATAGAGGAGAATATTATTGGTCAGGGCATCAAATAATGGCTTCTCCTGTAGGGTTTTCGGGGCCAGAATTCACTTTTCCGCTATATGGAACTATGGGAAA
----+----+----+----+----+----+----+----+----+----+----+----+----+----+----+----+----+----+----+----  1100
TATCTCCTCTTATAATAACCAGTCCCGTAGTTTATTACCGAAGAGGACATCCCAAAAGCCCCGGTCTTAAGTGAAAAGGCGATATACCTTGATACCCTTT r  g  e  y  y  w  s  g  h  q  i  m  a  s  p  v  g  f  s  g  p  e  f  t  f  p  l  y  g  t  m  g  n

F  B M              M                                          B  E  M  M
   N  A A              A                                          B  C  S  B
   U  V E              E                                          V  P  E  O
   H  1 2              1                                          2  1  1  2
   1

TGCAGCTCCACACAACGTATTGTTGCTCAACTAGGTCAGGGGGTCGTGTATAGAACATTATCGTCCACTTTATATAGAAGACCCTTTAATATAGGGATAAAT
----+----+----+----+----+----+----+----+----+----+----+----+----+----+----+----+----+----+----+----  1200
ACGTCGAGGTGTTGTTGCATAACAACGAGTTGATCCAGTCCCCCAGCACATATCTTGTAATAGCAGGTGAAATATATCTTCTGGAAAATTATATCCCTATTTA a  a  p  q  q  r  i  v  a  q  l  g  g  g  v  y  r  t  l  s  s  t  l  y  r  r  p  f  n  i  g  i  n
```

AATCAACAACTATCTGTTCTTGACGGGACAGAATTTGCTTATGGAACCTCCTCAAATTTGCCATCCGCTGTATACAGAAAAGCGAACGGTAGATTCGC
                                                                                                    1300
---+----+----+----+----+----+----+----+----+----+----+----+----+----+----+----+----+----+----+----
TTAGTTGTTGATAGACAAGAACTGCCCTGTCTTAAACGAATACCTTGGAGGAGTTTAAACGGTAGGCGACATATGTCTTTTCGCCTTGCCATCTAAGCG n  q  q  l  s  v  l  d  g  t  e  f  a  y  g  t  s  s  n  l  p  s  a  v  y  r  k  s  g  t  v  d  s  l

F           M           SABSEM          CT  M      N
              O           A           TVGECA          LA  S      L
              K           E           YRLCOE          AQ  E      A
              1           2           121111          11  1      3

TGGATGAAATACCGCCACAGAATAACAACGTGCCACCTAGGCAAGGATTTAGTCATCGATTAAGCCATGTTTCAATGTTCGTTCAGGCTTTAGTAATAG
                                                                                                    1400
---+----+----+----+----+----+----+----+----+----+----+----+----+----+----+----+----+----+----+----
ACCTACTTTATGGCGGTGTCTTATTGTTGCACGGTGGATCCGTTCCTAAATCAGTAGTAATTCGGTACAAAGCAAGTTACAAAGCAAGTCCGAAATCATTATC d  e  i  p  p  q  n  n  n  v  p  p  r  q  g  f  s  h  r  l  s  h  v  s  m  f  r  r  s  g  f  s  n  s
```

FIG. 7A3

```
A SHBN                                                                      M          MS
L SGAS                                                                      S          SP
U TINP                                                                      E          EO
1 1A22                                                                      1          11
   ///
TAGTGTAAGTATAATAAGAGCTCCTATGTTTCTCTTGGATACATCGTAGTGCTGAATTTAATAATATAATTCCTTCATCACAAATTACACAAATACCTTTA             1500
---.---+---.---+---.---+---.---+---.---+---.---+---.---+---.---+---.---+---.---+---.---+---.---+---.---+
ATCACATTCATATATTCTCGAGGATACAAGAGAGAACCTATGTAGCATCACGACTTAAATTATTATATTAAGGAAGTAGTGTTAATGTGTTTATGGAAAT
  s  v  s  i  i  r  a  p  m  f  s  w  i  h  r  s  a  e  f  n  n  i  i  p  s  s  q  i  t  q  i  p  l
---.---+---.---+---.---+---.---+---.---+---.---+---.---+---.---+---.---+---.---+---.---+
```

FIG. 7BI

MAPSEQ V5.10 PIC49INS.SEQ(1,2815) Reading frames: 1 Enzyme file ALL.ENZ

```
                                                                      M              ATH  X      E MASHCBH
                                         M   AAE AS  M                S              SAP  M      C BPCAFAA
                                         S   VSC PC  N                B              UQH  N      R OYRERLE
                                         E   AUR YR  L                O              211  1      2 2111113
                                         1   212 11  1                2              /         /    / ///
ACAAAATCTACTAATCTTGGCTCTGGAACTTCTGTCGTTAAAGGACCAGGATTTACAGGAGGAGATATTCTTGAAGAACTTCACCTGGCCAGATTTCAA
----+----+----+----+----+----+----+----+----+----+----+----+----+----+----+----+----+----+----+----+
TGTTTTAGATGATTAGAACCGAGACCTTGAAGACAGCAATTTCCTGGTCCTCCTCTATAAGAAGCTTCTTGAAGTGGACCGGTCTAAAGTT
                                                                                              1600 t  k  s  t  n  l  g  s  g  t  s  v  v  k  g  p  g  f  t  g  g  d  i  l  r  r  t  s  p  g  q  i  s  t

E      H
                            C      N
                            R      F
                            V      3
                            1
                                                                                                      +

A M                                                                                         B  B
 F S       S S                                                                                B  V
 L E       S P                                                                                2
 2 1       P 1
           1
CCTTAAGAGGTAAATATTACTGCACCATTATCACAAAGATATCGGGTAAGAATTCGCTACGCTTCTACCACAAATTTACAATTCCATACATCAATTGACGG
----+----+----+----+----+----+----+----+----+----+----+----+----+----+----+----+----+----+----+----+
GGAATTCTCATTTATAATGACGTGGTAATAGTGTTTCTATAGCCCATTCTTAAGCGATGCGAAGATGGTGTTTAAATGTTAAGGTATGTAGTTAACTGCC
                                                                                               1700 l  r  v  n  i  t  a  p  l  s  q  r  y  r  v  r  i  r  y  a  s  t  t  n  l  q  f  h  t  s  i  d  g
```

FIG. 7B2

```
                                                              BH  H A
       E  AM M                                                SP  I L
       C  SS B                                                PA  N U
       P  EE O                                                22  3 1
       1  11 2                                                 |  | |
AAGACCTATTAATCAGGGGAATTTTTCAGCAACTATGAGTAGTGGGAGTAGTAATTTACAGTCCGGAAGCTTTAGGACTGTAGGTTTTACTACTCCGTTTAAC
---+---------+---------+---------+---------+---------+---------+---------+---------+---------+---------+  1800
TTCTGGATAATTAGTCCCCTTAAAAGTCGTTGATACTCATCATCACCCTCATTAAATGTCAGGCCTTCGAAATCCTGACATCCAAATGATGAGGCAAATTG r   p  i  n  q  g  n  f  s  a  t  m  s  s  g  s  n  l  q  s  g  s  f  r  t  v  g  f  t  t  p  f  n

M  M  HN N  B                           M DTH         X  H   M M
        BM D          M  M  M    A  B  GS L  B                           B PAN         M  P   A N
        IB P          A  S  E    E  O  IP A  V                           O NQF         N  A   E L
        NO N          E  E  L    2  2  A2 3  2                           1 113         1  2   3 1
        11 1          2  1                                                 |  |        |  |     |
TTTCAAATGGATCAAGTGTATTACGTTAAGTGCTCATGTCTTCAATTCAGGCAATGAAGTTTATATAGATCGAATTGAATTTGTTCCGGCAGAAGTAA
---+---------+---------+---------+---------+---------+---------+---------+---------+---------+---------+  1900
AAAGTTTACCTAGTTCACATAAATGCAATTCACGAGTACAGAAGTTAAGTCCGTTACTTCAAATATATCTAGCTTAACTTAAACAAGGCCGTCTTCATT f  n  g  s  s  v  f  t  l  s  a  h  v  f  n  s  g  n  e  v  y  i  d  r  i  e  f  v  p  a  e  v  t
```

FIG. 7B3

```
                              A MH                              M
                              L BP                              S    M
                              U OH                              E    A  E
                              1 21                              1       3
CCTTTGAGGCAGAATATGATTTAGAAAGAGCACAAAAGGGCGGTGAATGAGCTGTTTACTTCTTCCAATCAAATCGGGTTAAAAACAGATGTGACGGATTA
---+---------+---------+---------+---------+---------+---------+---------+---------+---------+----  2000
GGAAACTCCGTCTTATACTAAATCTTTCTCGTGTTTTCCGCCACTTACTCGACAAATGAAGAAGGTTAGTTAGCCCAATTTTTGTCTACACTGCCTAAT f e a e y d l e r a q k a v n e l f t s s n q i g l k t d v t d y
```

FIG. 8AI

MAPSEQ V5.10 PIC49INS.SEQ(1,2815) Reading frames: 1 Enzyme file ALL.ENZ

```
                                                                        F           N N    D
BMD                                                                     O           S L    D
CBP                                                                     K           P A    E
LON                                                                     1           H 3    1
111                                                                     /           /
TCATATTGATCAAGTATCCAATTTAGTTGAGTGTTTATCTGATGAATTTTGTCTGGATGAAAAAAAAGAATTGTCCGAGAAAGTCAAACATGCCGAACGAC   2100
----+----+----+----+----+----+----+----+----+----+----+----+----+----+----+----+----+----+----+----+
AGTATAACTAGTTCATAGGTTAAATCAACTCACAAATAGACTACTTAAAACAGACCTACTTTTTTTTCTTAACAGGCTCTTTCAGTTTGTACGCTTGCTG h  i  d  q  v  s  n  l  v  e  c  l  s  d  e  f  c  l  d  e  k  k  e  l  s  e  k  v  k  h  a  n  d

XMD  BM         BM D          M  SE M                                 F R       M SS
    HBP  IN         IB P          A  EC N                                 O S       N TE
    OON  NL         NO N          E  CP L                                 K A       L YC
    211  11         111           1  11 1                                 1 1       1 11
    /                                                                               /
TTAGTGATGAGCGGAATTTACTTCAAGATCCAAACTTTAGAGGGATCAATAGACACAACTAGACCGTGGCTGGAGAGAGAAGTACGGATATTACCATCCAAGG   2200
----+----+----+----+----+----+----+----+----+----+----+----+----+----+----+----+----+----+----+----+
AATCACTACTCGCCTTAAATGAAGTTCTAGGTTTGAAATCTCCCTAGTTATCTGTTGATCTGGCACCGACCTCTCCTTCATGCCTATAATGGTAGGTTCC l  v  m  s  g  l  y  f  k  i  q  t  l  l  e  g  s  i  d  n  .  t  v  a  g  e  e  v  r  i  l  p  s  k  e
```

FIG. 8A2

```
                    M                                      M                              H  T  PM
                    A          BANRK                       A                              N  A  LS
                    E          ASLSP                       E                              F  Q  EE
                    2          NPAAN                       2                              1  1  11
                               11411
                               / /
AGGCGATGACGTATTCAAAGAGAATTACGCTTACGGCTATTGGGTACCTTTGATGAGTGCTATCCAACGTATTATATCAAAAAAATAGATGAGTCGAAATTA
----+----+----+----+----+----+----+----+----+----+----+----+----+----+----+----+----+----+----+----+   2300
TCCGCTACTGCATAAGTTTCTCTTAATGCAATGCGATAACCCATGGAAACTACTCACGATAGGTTGCATAAATAGTTTTTATCTACTCAGCTTTAAT a  m  t  y  s  k  r  i  t  l  r  y  w  v  p  l  m  s  a  i  q  r  i  y  i  k  k  .  m  s  r  n  .

M  M  M                      T               M  D                          M   H
          A  N  S                      A               B  D                          S   N
          E  L  E                      Q               O  E                          E   F
          3  1  1                      1               2  1                          1   3

AAAGCCTATACCCGTTACCAATTAAGAGAGGGTATATCGAAGATAGTCAAGACTTAGAAATCTATTTAATTCGCTACAATGCCAAACACGAAACAGTAAATG
----+----+----+----+----+----+----+----+----+----+----+----+----+----+----+----+----+----+----+----+   2400
TTTCGGATATGGGCAATGGTTAATTCTCCCATATAGCTTCTATCAGTTCTGAATCTTTAGATAAATTAAGCGATGTTACGGTTTGTCTTTGTCATTTAC k  p  i  p  v  t  n  .  e  g  i  s  k  i  v  k  t  .  k  s  i  .  f  a  t  m  p  n  t  k  q  .  m
```

FIG. 8A3

```
E  AS   R      N      GCHF                    N              SS T
C  PC   S      L      DFAN                    S              TE T
R  YR   A      A      IREU                    P              YC H
2  11   1      4      213H                    2              11 2
                       /                                      /
TGCCAGGTACGGGGTTCCTTATGGCCGCTTTCAGCCCCAAGTCCAATCGGAAAATGTGCCATCATTCCCATCATTCCTCCTTGGACATTGATGTTGGATG
---+---------+---------+---------+---------+---------+---------+---------+---------+---------+    2500
ACGGTCCATGCCCAAGGAATACCGGCGAAAGTCGGGGTTCAGGTTAGCCTTTTACACGGGTAGTAAGGGTAGTAAGAGGAACCTGTAACTACAACCTAC c  q  v  r  v  p  y  g  r  f  q  p  q  v  q  s  e  n  v  p  i  i  p  i  i  s  p  w  t  l  m  l  d  v
```

FIG. 8BI

MAPSEQ V5.10 PIC49INS.SEQ(1,2815) Reading frames: 1  Enzyme file ALL.ENZ

```
R    M  MF        D             H M       HCHBH  N     M        XM        TKE
S    N  SO        D             P S       GFAAA  L     A        BA        ASA
A    L  EK        E             H E       ARELE  A     E        AE        QPR
1    1  11        1             1 1       11113  3     1        11        121
                                                //                         //
    TACAGACTTAAATGAGGACTTAGGTGTATGGGTGTGATATATTCAAGATTAAGACGCAAGATGGCCATGCAAGACTAGGAAATCTAGAATTTCTGAAGAGAAA
            2600
    ATGTCTGAATTTACTCCTGAATCCACATACCCACTATAAGTTCTAATTCTGCGTTCTACCGGTACGTTCTGATCCTTAGATCTTAAAGAGCTTCTCTTT q  t  .  m r t  .  v y g .  y s r l r r k m a m q d .  e i .  n f s k r n

B                M                          S       M
                                 S          M     A                          S       N
                                 M          L     E                          P       L
                                 2          1     1                          1       1
    CCATTAGTAGGAGAAGCACTAGCTCTCGTGTGAAAAGAGCGGAGAGACAAACGTGAAAAATTGGAATGGGAAACAAATATTGTTATAAAG
                                                                                        2700
    GGTAATCATCCTCTCGTGATCGAGCACACTTTTCTCGCCCTCTTTTTAACCTTTTACCTTTGTTGCACTTTTTAACCTTTATAACAAATATTTC h .  .  e k h .  l v .  k e r r k n g e t n v k n w n g k q i l f i k
```

FIG. 8B2

```
                                              NT    H T    NF              MAT
                                              RH    N T    LN              LFH
     SH                                       UA    F H    AU              ULA
     FN                                       1 1   1 2    3H              131
     AF                                                                           2800
     N1
AGGCAAAGAATCTGTAGATGCTTTATTTGTAAACTCTCAATATGATAGATTACAAGCGGATACCAACATCGCGATGATTCATGCGGCAGATAAACGCGT
---:-:--:---:--:-+--:-----:--:-+-:------:-----+-------:---:---:+-----:-:---:---+---:-:----:--:-.:+
TCCGTTTCTTAGACATCTACGAAATAAACATTTGAGAGTTATACTATCTAATGTTCGCCTATGGTTGTAGGCTACTAAGTACGCCGTCTATTTGCGCA r  q  k  n  l  .  m  l  y  l  .  t  l  n  m  i  d  y  k  r  i  p  t  s  r  .  f  m  r  q  i  n  a  f

B    T H
   S    A N
   M    Q F
   1    1 3
TCATAGCATTCGAGA
---:-+--:-----.    2815
AGTATCGTAAGCTCT i  a  f  e  k
```

FIG. 9AI

```
MAPSEQ V5.10 CHIM-B-A.SEQ(1,3066) Reading frames: 3  Enzyme file ALL.ENZ

S  D       H  N  P  MD
MHH  SEASS                               P  R       N  D  L  SR
SPI  ECPCE                               O  A       F  E  E  EA
EAN  CRYRC                               1  3       1  1  1  11
112  12111
   / //
GTTAACACCCCTGGGTCAAAAATTAGTAAAAATTGATATATTTAGTTGCACTTTGTGCATTTTTTCATAAGATGAGTCATATGTTTAAATTGTAGTAATGAAA
----+----+----+----+----+----+----+----+----+----+----+----+----+----+----+----+----+----+----+----+  100
CAATTGTGGGACCCAGTTTTTAATCATTTTTAACTATAAATCATTTTAATCAACGTAAAAAAGTATTCTACTCAGTATACAAAATTTAACATCATTACTTT

. h p g s k i d i . . n . l h f v h f f i r . v i c f k l . . k

M  M                           XBBNA
                                        S  N                           MSSSV
                                        E  A                           NMMIA
                                        1  E                           11113
                                           3                              / //
AACAGTATTATATCATAATGAATTGGTATCTTAATAAAAGAGATGAGGTAACTTATGGATAACAATCCGAACATCAATGAATGCATTCCTTATATAATTGT
----+----+----+----+----+----+----+----+----+----+----+----+----+----+----+----+----+----+----+----+  200
TTGTCATAATATAGTATTACTTAACCATAGAATTATTTTCTCTACCTCCATTGAATACCTATTGTTAGTTACTTACGTAAGGAATATTAACA t v l y h n e l v s . . k r w r . l m d n n p n f n e c i p y n c
```

FIG. 9A2

```
                            M B         C T
         M                  A S         L A
         S                  E R         A Q
         E                  3 1         1 1
         1
         3
TTAAGTAACCCTGAAGTAGAAGTATTAGGTGGAGAAAGAAGATAGAAACTGGTTACACCCCAATCGATATTTCCTTGTCGCTAACGCAATTCTTTTGAGTG
     ---------+---------+---------+---------+---------+---------+---------+---------+---------+---------+   300
AATTCATTGGGACTTCATCTTCATAATCCACCTCTTTCTTATCTTTGACCAATGTGGGGTTAGCTATAAAGGAACAGCGATTGCGTTAAAGAAAACTCAC l  s  n  p  e  v  e  v  l  g  g  e  r  i  e  t  g  y  t  p  i  d  i  s  l  s  l  t  q  f  l  l  s  e

X T    N S H              S M              A A N F            M F    H R
            M T    C C P              P A              V S L I            N I    G S
            N H    I R A              E E              A U A N            L N    A A
            1 2    1 1 2              1 1              2 1 4 1            1 1    1 1
AATTTGTTCCCGGTGCTGTGGATTTGTGTTAGGACTAGTTGATATAATATGGGGAATTTTTGGTCCCTCTCAATGGGACGCATTCTTGTACAAATTGAACA
     ---------+---------+---------+---------+---------+---------+---------+---------+---------+---------+   400
TTAAACAAGGGCCACGACACCTAAACACAATCCTGATCAACTATATTATACCCCTTAAAAACCAGGAGAGTTACCCTGCGTAAAGAACATGTTTAACTTGT f  v  p  g  a  g  f  v  l  g  l  v  d  i  i  w  g  i  f  g  p  s  q  w  d  a  f  l  v  q  i  e  q
```

FIG. 9B1

MAPSEQ V5.10 CHIM-B-A.SEQ(1,3066) Reading frames: 3  Enzyme file ALL.ENZ

```
                E        HM M  N                         XM         D      H
                C        NA B  L                         BA         D      N
                R        FE O  A                         AE         E      F
                1        31 2  4                         11         1      1
GTTAATTAACCAAGAATAGAAGAATTCGCTAGGAACCAAGCCATTCTAGATTAGAGGACTAAGCAATCTTTATCAAATTTACGCAGAATCTTTTAGA    500
----+----|----+----|----+----|----+----|----+----|----+----|----+----|----+----|----+----|----+
CAATTAATTGGTTCTTATCTTCTTAAGCGATCCTTGGTTCGGTAAAGATCTAATCTTCCTGATTCGTTAGAAATAGTTTAAATGCGTCTTAGAAAATCT l i n q r i e e f a r n q a i s r l e g l s n l y q i y a e s f r

MS KE       T  M                   N
              XMD B                 SF SA       T  B                   L   N   S
              HBP I                 EA PR       H  O                   A   P
              OON N                 1N 21       2  2                   3   2
GAGTGGGAAGCAGATCCTACTAATCCAGCATTAAGAGAAGAGATGCGTATTCAATTCAATGACATGAACAGTGCCCTTACAACCGCTATTCCTCTTTTG    600
----+----|----+----|----+----|----+----|----+----|----+----|----+----|----+----|----+----|----+
CTCACCCTTCGTCTAGGATGATTAGGTCGTAATTCTCTTCTCTACGCATAAGTTACTGTACTTGTCACGGGAATGTTGGCGATAAGGAGAAAAAC e w e a d p t n p a l r e e m r i q f n d m n s a l t t a i p l f a
```

FIG. 9B2

```
                            MB                      AF                                            S
                            NB                      LN                                            F
                            LV                      UU                                            A
M                           11                      1H                                            N
N
L
1
CAGTTCAAAATTATCAAGTCCTCTTTTATCAGTATGTTCAAGCTGCAAATTTACATTTATCAGTTTTGAGAGATGTTCAGTGTTTGGACAAAGGTG
----+----+----+----+----+----+----+----+----+----+----+----+----+----+----+----+----+----+----+   700
GTCAAGTTTTAATAGTTCAAGGAGAAAATAGTCATATACAAGTTCGACGTTTAAATGTAAATAGTCAAAACTCTCTACAAGTCACAAACCTGTTTCCAC v  q  n  y  q  v  p  l  l  s  v  y  y  q  a  a  n  l  h  l  s  v  l  r  d  v  s  v  f  g  q  r  w
-+----+----+----+----+----+----+----+----+----+----+----+----+----+----+----+----+----+----+----+

F T                       M M               M D        N    R        R
         N H                       S A               B P        L    S        S
         U A                       E E               O N        A    A        A
         H 1                       1 1               1 1        1    3        1
GGGATTTGATGCCGCGACTATCAATAGTCGTTATAATGATTTAACTAGGCTTATTGGCAACTATACAGATCATGCTGTACGCTGGTACAATACGGGATTA
----+----+----+----+----+----+----+----+----+----+----+----+----+----+----+----+----+----+----+    800
CCCTAAACTACGGCGCTGATAGTTATCAGCAATATTACTAAATTGATCCGAATAACCGTTGATATGTCTAGTACGACACATGCGACCATGTTATGCCCTAAT g  f  d  a  a  t  i  n  s  r  y  n  d  l  t  r  l  i  g  n  y  t  d  h  a  v  r  w  y  n  t  g  l
-+----+----+----+----+----+----+----+----+----+----+----+----+----+----+----+----+----+----+----+
```

FIG. IOAI

MAPSEQ V5.10 CHIM-B-A.SEQ(1,3066)  Reading frames: 3  Enzyme file ALL.ENZ

```
ANAFH H    XM                   KE           E
VLSIP N    BA                   SA   M  M    C
AAUNA F    AE                   PR   S  B    R
24112 1    11                   21   E  O    V
                                     1  2
```

```
GAGGCGTGTATGGGGACCGGATTCGAGAGATTGGATAAGATATAATCAATTTAGAAGAGAATTAACACTAACTGTATTAGATATCGTTTCTATTTCCGA
----+----|----+----|----+----|----+----|----+----|----+----|----+----|----+----|----+----|----+----|  900
CTCGCACATACCCCTGGCCTAAGATCTCTAACCTATTCTATATTAGTTAAATCTTCTCTTAAATTGTGATTGACATAATCTATAGCAAAGATAAAGGCT
``` e  r  v  w  g  p  d  s  r  d  w  i  r  y  n  q  f  r  r  e  l  t  l  t  v  l  d  i  v  s  l  f  p  n

```
         ATH    X           M
         SAN    M           S
         UQF    N           E
         213    1           1
```

```
         M
         A
         E
         2
```

```
ACTATGATAGTAGTAGAACGTATCCAATTCGAACAGTTTCCCAATTAACAAGAGAAATTTATACAAACCCAGTATTAGAAAATTTTGATGGTAGTTTCGAGG
----+----|----+----|----+----|----+----|----+----|----+----|----+----|----+----|----+----|----+----|  1000
TGATACTATCATCTTGCATAGGTTAAGCTTGTCAAAGGGTTAATTGTTCTCTTTAAATATGTTTGGGTCATAATCTTTTAAAACTACCATCAAAAGCTCC
```

```
           D            H   P        M   S S        M   F  S
           D            N   L        S   P F        N   O  S
           E            F   E        E   O A        L   K  P
           1            1   1        1   1 N        1   1  1
CTCGGCTCAGGGCATAGAAGGAAGTATTAGGAGTCCACATTTGATGGATATACTTAACAGTATAACCATCTATACGGATGCTCATAGAGGAGAATATTAT 1100
---+----:----+----:----+----:----+----:----+----:----+----:----+----:----+----:----+----:----+----:
GAGCCGAGTCCCGTATCTTCCTTCATAATCCTCAGGTGTAAACTACCTATATGAATTGTCATATTGGTAGATATGCCTACGAGTATCTCCTCTTATAATA s  a  q  g  i  e  g  s  i  r  s  p  h  l  m  d  i  l  n  s  i  t  i  y  t  d  a  h  r  g  e  y  y

F  A         B  M
              S                        A N H     E                  N  L         B  A
              F                        S L A     C                  U  U         V  E
              A                        U A E     R                  H  1         1  2
              N                        1 4 3     1
TGGTCAGGGCATCAAATAATGGCTTCTCCTCCTGTAGGGTTTTCGGGGCCAGAATTCACTTTTCCGCTATATGGAACTATGGAAATGCAGCTCCACAACAAC 1200
---+----:----+----:----+----:----+----:----+----:----+----:----+----:----+----:----+----:----+----:
ACCAGTCCCGTAGTTTATTACCGAAGAGGACATCCCAAAAGCCCCGGTCTTAAGTGAAAAGGCGATATACCCTTGATACCCTTTACGTCGAGGTGTTGTTG w  s  g  h  q  i  m  a  s  p  v  g  f  s  g  p  e  f  t  f  p  l  y  g  t  m  g  n  a  a  p  q  q  r
```

FIG. 10B1

```
MAPSEQ V5.10 CHIM-B-A.SEQ(1,3066) Reading frames: 3  Enzyme file ALL.ENZ

B  E M M
          M                                     B  C S B
          A                                     V  P E O
          E                                     2  1 1 2
          1
GTATTGTTGCTCAACTAGGTCAGGGCGTGTATAGAACATTATCGTCCACTTTATATAGAAGACCTTTTAATATAGGGATAAATAATCAACAACTATCGT      1300
----+----|----+----|----+----|----+----|----+----|----+----|----+----|----+----|----+----|----+----|
CATAACAACGAGTTGATCCAGTCCCGCACATATCTTGTAATAGCAGGTGAAATATATCTTCTGGAAAATTATATCCCTATTTATTAGTTGTTGATAGACA
 i  v  a  q  l  g  q  g  v  y  r  t  l  s  s  t  l  y  r  r  p  f  n  i  g  i  n  n  q  q  l  s  v

F        N F        M M  N S A                            H  H           F
             I        L O        N N  S N C                            N  N           O
             N        A K        L L  P A C                            F  F           K
             1        4 1        1 1  B 1 1                            1  3           1
TCTTGACGGGACAGAATTTGCTTATGGAACCTCCTCAAATTTGCCATCCGCGTATACAGAAAAAGCGGAACGGTAGATTCGCTGGATGAAATACCGCCA      1400
----+----|----+----|----+----|----+----|----+----|----+----|----+----|----+----|----+----|----+----|
AGAACTGCCCTGTCTTAAACGAATACCTTGGAGGAGTTTAAACGGTAGGCGACATATGTCTTTTCGCCTTGCCATCTAAGCGACCTACTTTATGGCGGT
 l  d  g  t  e  f  a  y  g  t  s  s  n  l  p  s  a  v  y  r  k  s  g  t  v  d  s  l  d  e  i  p  p
----+----|----+----|----+----|----+----|----+----|----+----|----+----|----+----|----+----|----+----|
```

```
MAPSEQ V5.10 CHIM-B-A.SEQ(1,3066) Reading frames: 3   Enzyme file ALL.ENZ

M     AAE AS  M      M        ATH  X     E MASHCBH       AM        S
    S     VSC PC  N      B        SAP  M     C BPCAFAA       FS        S
    E     AUR YR  L      O        UQH  N     R OYRERLE       LE        P
    1     212 11  1      2        211  1     2 2111113       21        1
        /            /                  /           ////
TGGCTCTGGAACTTCTGTCGTTAAAGGACCAGGATTTACAGGAGGAGATATTCTTGAAGAACTTCACCTGGCCAGATTTCAACCTTAAGAGTAAATATT
---+---------+---------+---------+---------+---------+---------+---------+---------+---------+  1700
ACCGAGACCTTGAAGACAGCAATTTCCTGGTCCTCCTCTATAAGAACTTCTTGAAGTGGACCGGTCTAAAGTTGAATTCTCATTTATAA g s g t s v v k g p g f t g g d i l r r t s p g q i s t l r v n i

E        H
                   C        N
                   R        F
                   V        3
                   1
                                                                             B    E   AM M
                                                                             B    C   SS B
                                                                             V    P   EE O
                                                                             2    1   11 2
                                                                                         /
ACTGCACCATTATCACAAAGATATCGGGTAAGAATTCGCTACGCTTCTACCACAAATTTACAATTCCATACATCAATTGACGGAAGACCTATTAATCAGG
---+---------+---------+---------+---------+---------+---------+---------+---------+---------+  1800
TGACGTGGTAATAGTGTTTCTATAGCCCATTCTTAAGCGATGCGAAGATGGTGTTTAAATGTTAAGGTATGTAGTTAACTGCCTTCTGGATAATTAGTCC t a p l s q r y r v r i r y a s t t n l q f h t s i d g r p i n q g
```

FIG. IIA2

FIG. 11B1

```
MAPSEQ V5.10 CHIM-B-A.SEQ(1,3066) Reading frames: 3  Enzyme file ALL.ENZ

HN                      A MH              M              M           BMD
     GS                      L BP              S              A           CBP
     IP                      U OH              E              E           LON
     A2                      1 21              1              3           111
      /                       /                                             /
GATTTAGAAAGAGCACAAAAGGCGGTGAATGAGCTGTTACTTCTTCCAATCAAATCGGGTTAAAAACAGATGTGACGGATTATCATATTGATCAAGTAT
----+----+----+----+----+----+----+----+----+----+----+----+----+----+----+----+----+----+----+----   2100
CTAAATCTTTCTCGTGTTTTCCGCCACTTACTCGACAAATGAAGAAGGTTAGTTTAGCCCAATTTTTGTCTACACTGCCTAATAGTATAACTAGTTCATA d  l  e  r  a  q  k  a  v  n  e  l  f  t  s  s  n  q  i  g  l  k  t  d  v  t  d  y  h  i  d  q  v  s

F                             NN    D
                                 O                             SL    D
                                 K                             PA    E
                                 1                             H3    1
                                 /                              /
CCAATTTAGTTGAGTGTTTATCAGATGAATTTTGTCTGGATGAAAAACAAGAATTGTCCGAGAAAGTCAAACATGCGAAGCGACTTAGTGATGAGCGGAA
----+----+----+----+----+----+----+----+----+----+----+----+----+----+----+----+----+----+----+----   2200
GGTTAAATCAACTCACAAATAGTCTACTTAAACAGACCTACTTTTTGTTCTTAACAGGCTCTTTCAGTTGTACGCTTCGCTGAATCACTACTCGCCTT n  l  v  e  c  l  s  d  e  f  c  l  d  e  k  q  e  l  s  e  k  v  k  h  a  k  r  l  s  d  e  r  n
```

FIG.11B2

```
         XMD BM      BM D           M   SE M     F R         M SS           M
         HBP IN      IB P           A   EC N     O S         N TE           A
         OON NL      NO N           E   CP L     K A         L YC           E
         211 11      11 1           1    11 1    1 1         1 11           2

TTTACTTCAAGATCCAAACTTCAGAGGATCAATAGACAACTAGACCGTGGCTGAGAGGAAGTACGGATATATTACCATCCAAGGAGGCGATGACGTATTC
------+---------+---------+---------+---------+---------+---------+---------+---------+---------+     2300
AAATGAAGTTCTAGGTTTGAAGTCTCCCTAGTTATCTGTTGATCTGGCACCGACCTCTCCTTCATGCCTATAATGGTAGGTTCCTCCGCTACTGCATAAG l  l  q  d  p  n  f  r  g  i  n  r  q  l  d  r  g  w  r  g  s  t  d  i  t  i  q  g  g  d  d  v  f
------+---------+---------+---------+---------+---------+---------+---------+---------+---------+

MM     BANRK                M                        H T         PM
         AA     ASLSP                A                        N A         LS
         EE     NPAAN                E                        F Q         EE
         23     11411                2                        1 1         11

AAAGAGAATTACGTTACGCTATTGGGTACCTTTGATGAGTGCTATCCAACGTATTTATATCAAAAAATAGATGAGTCGAAATTAAAGCCTATACCCGTT
------+---------+---------+---------+---------+---------+---------+---------+---------+---------+     2400
TTTCTCTTAATGCAATGCGATAACCCATGGAAACTACTCACGATAGGTTGCATAAATAGTTTTTATCTACTCAGTTTAATTTTCGGATATGGGCAA k  e  n  y  v  t  l  l  g  t  f  d  e  c  y  p  t  y  l  y  q  k  i  d  e  s  k  l  k  a  y  t  r  y
------+---------+---------+---------+---------+---------+---------+---------+---------+---------+
```

FIG. 12A1

MAPSEQ V5.10 CHIM-B-A.SEQ(1,3066) Reading frames: 3 Enzyme file ALL.ENZ

```
M   T       M   M H       N           E  AS  R N
N   A       B   S N       L           C  PC  S L
S   Q       D   E F       A           R  YR  A A
E   1       O   1 3       3           2  11  1 4
L   1       E                            1
1           2
            1
ATCAATTAAGAGAGGGTATATCGAAGATAGTCAAGACTTAGAAAATCTATTTAATTCGCTACAATGCAAAACATGAAACATGAAACAGTAAATGTGCCAGGTACGGGTTC  2500
----+----+----+----+----+----+----+----+----+----+----+----+----+----+----+----+----+----+----+----+----+----+
TAGTTAATTCTCTCCCATATAGCTTCTATCAGTTCTGAATCTTTTAGATAAATTAAGCGATGTTACGTTTTGTACTTTGTCATTTACACGGTCCATGCCCAAG q  l  r  g  y  i  e  d  s  q  d  l  e  i  y  l  i  r  y  n  a  k  h  e  t  v  n  v  p  g  t  g  s

S H H CT  HBHTHH              H   D
                    F N N LA  ISHHHI              N   D
                    A F F AQ  NSAAAN              F   E
           GCHF     N 3 1 11  P2111P              1   1
           DFAN
           IREU
           213H
CTTATGGCCGCTTTCAGCCCAAAGTCCAATCGGAAAGTGTGGAGAGCCGAATCGATGCGCCACACCTTGAGTGGAATCCTGACTTAGATTGTTCGTGT  2600
----+----+----+----+----+----+----+----+----+----+----+----+----+----+----+----+----+----+----+----+
GAATACCGGCGAAAGTCGGGTTTCAGGTTAGCCTTTCACACCTCTCGGCTTAGCTACGCGCCGGTGTGGAACTCACCTTAGGACTGAATCTAACAAGCACA l  w  p  l  s  a  q  s  p  i  g  k  c  g  e  p  n  r  c  a  p  h  l  e  w  n  p  d  l  d  c  s  c
```

FIG. 12A2

```
RESIDUES ANALYZED : 970                          WINDOW SIZE :  HOPP    7
                                                                KYTE    9
FIRST PASS MADE: YES                             pH:  7.000

ROBSON                                           CHOU-FASMAN
CONFORMATION --  HELIX       1%                  CONFORMATION :  HELIX     15%
                 EXTENDED   60%                                  EXTENDED  75%
                 TURN       30%                                  TURN      39%
                 COIL       10%

Robson Decision Constants:
HELIX  EXTEND  TURN  COIL
 158    -88      0     0

ANTIGENIC SITES :  COORDINATE   HOPP INDEX :
                      861          2.13
                      405          1.77
                      597          1.64
                      860          1.63
                      882          1.61

MOLECULAR WT:  TOTAL     102919 g/mol            AVE HYDROPHOBICITY :  HOPP (-100X)    5
               AVERAGE      106 g/mol                                  KYTE ( 100X)  -40

ISOELECTRIC PT :  pH = 10.29

AMINO ACID DISTRIBUTION :
RESIDUE   NUMBER  PERCENT                        RESIDUE   NUMBER  PERCENT
Ala (A)     28      3%                           Phe (F)     52      5%
Arg (R)    102     11%                           Pro (P)     24      2%
Asn (N)     46      5%                           Ser (S)    115     12%
Asp (D)     15      2%                           Thr (T)     45      5%
Cys (C)     52      5%                           Trp (W)     20      2%
Glu (E)     22      2%                           Tyr (Y)     50      5%
Gln (Q)     23      2%                           Val (V)     32      3%
Gly (G)     45      5%                           Asx (B)      0      0%
His (H)     18      2%                           Glx (Z)      0      0%
Ile (I)     64      7%                           Ter (-)     94     10%
Leu (L)     56      6%                           Xxx (X)      0      0%
Lys (K)     56      6%                           ??? (?)      0      0%
Met (M)     11      1%
```

FIG. 13

```
RESIDUES ANALYZED :    696                    WINDOW SIZE : HOPP    7
                                                            KYTE    9
FIRST PASS MADE: YES                          pH:   7.000

ROBSON                                        CHOU-FASMAN
CONFORMATION :  HELIX        5%               CONFORMATION :  HELIX     33%
                EXTENDED    62%                               EXTENDED  68%
                TURN        13%                               TURN      33%
                COIL        20%

Robson Decision Constants :
HELIX  EXTEND  TURN  COIL
 158    -88     0     0

ANTIGENIC SITES :  COORDINATE    HOPP INDEX :
                      665           1.93
                      666           1.93
                      667           1.93
                      663           1.74
                      664           1.63

MOLECULAR WT:  TOTAL     77964 g/mol    AVE HYDROPHOBICITY :    HOPP (-100X)   15
               AVERAGE     112 g/mol                            KYTE ( 100X)  -26

ISOELECTRIC PT:  pH = 5.39

AMINO ACID DISTRIBUTION :
RESIDUE  NUMBER PERCENT              RESIDUE  NUMBER PERCENT
Ala (A)    34     5%                 Phe (F)    39     6%
Arg (R)    44     6%                 Pro (P)    34     5%
Asn (N)    49     7%                 Ser (S)    71    10%
Asp (D)    31     4%                 Thr (T)    46     7%
Cys (C)     4     1%                 Trp (W)     9     1%
Glu (E)    38     5%                 Tyr (Y)    27     4%
Gln (Q)    35     5%                 Val (V)    44     6%
Gly (G)    49     7%                 Asx (B)     0     0%
His (H)    12     2%                 Glx (Z)     0     0%
Ile (I)    51     7%                 Ter (-)     1     0%
Leu (L)    58     8%                 Xxx (X)     0     0%
Lys (K)    10     1%                 ??? (?)     0     0%
Met (M)    10     1%
```

FIG. 14.

```
RESIDUES ANALYZED :    969                      WINDOW SIZE :  HOPP    7
                                                               KYTE    9
FIRST PASS MADE:  YES                           pH:   7.000

ROBSON
CONFORMATION:   HELIX     24%                   CHOU-FASMAN
                EXTENDED  48%                   CONFORMATION:  HELIX     38%
                TURN      14%                                  EXTENDED  64%
                COIL      14%                                  TURN      32%

Robson Decision Constants:
HELIX  EXTEND  TURN  COIL
 -75    -88     0     0

ANTIGENIC SITES:  COORDINATE   HOPP INDEX:
                     890         2.31
                     891         2.31
                     886         2.09
                     887         2.09
                     888         2.09

MOLECULAR WT:  TOTAL    109784 g/mol            AVE HYDROPHOBICITY :    HOPP (-100X)    4
               AVERAGE     113 g/mol                                    KYTE ( 100X)  -41

ISOELECTRIC PT:  pH = 5.69

AMINO ACID DISTRIBUTION:
RESIDUE  NUMBER PERCENT                RESIDUE  NUMBER PERCENT
Ala (A)    51    5%                    Phe (F)    47    5%
Arg (R)    64    7%                    Pro (P)    44    5%
Asn (N)    61    6%                    Ser (S)    84    9%
Asp (D)    52    5%                    Thr (T)    59    6%
Cys (C)    13    1%                    Trp (W)    16    2%
Glu (E)    62    6%                    Tyr (Y)    38    4%
Gln (Q)    47    5%                    Val (V)    57    6%
Gly (G)    65    7%                    Asx (B)     0    0%
His (H)    24    2%                    Glx (Z)     0    0%
Ile (I)    65    7%                    Ter (-)     1    0%
Leu (L)    83    9%                    Xxx (X)     0    0%
Lys (K)    27    3%                    ??? (?)     0    0%
Met (M)    10    1%
```

FIG. 15.

DNA CONSTRUCTS ENCODING *BACILLUS THURINGIENSIS* TOXINS FROM STRAIN A20

This invention relates to recombinant DNA, and in particular to such DNA coding *Bacillus thuringiensis* endotoxin.

The organism *Bacillus thuringiensis* carries genes which encode protein endotoxins which are insecticidal to a variety of agronomically important insects. They are not however harmful to many benign insects, or to earthworms, birds, fish or mammals. These endotoxins are thus useful as agricultural insecticides, particularly against Lepidopteran pests. *Bacillus thuringiensis* strains have been used as agricultural insecticides for many years.

Recently, *Bacillus thuringiensis* endotoxin genes have been engineered into dicotyledonous plants and shown to confer protection against insect attack. The *Bacillus thuringiensis* kurstaki strain, A20, is the subject of our prior unpublished copending UK application No 8730132 filed 24 Dec. 1987. Strain A20 has been deposited at the National Collection of Industrial and Marine Bacteria (NCIMB) at Aberdeen, Scotland on 20 Oct. 1987 under the NCIMB Accession Number 12570. It is more active than the commonly used variety kurstaki strain, HD-1. Strain A20 carries three different, but highly related, endotoxin genes similar to those described in the scientific literature as 6.6-, 5.3-, and 4.5-type genes. The first two genes are carried in one or more copies on plasmids and also on the bacterial chromosome, while the 4.5- type gene is only found on the bacterial chromosome.

According to the present invention we provide recombinant DNA coding for an insecticidally active form of the *Bacillus thuringiensis* endotoxin which DNA is derived from the A20 strain of *Bacillus thuringiensis*. The source of the DNA maybe either the chromosome or a plasmid.

In a further aspect, our invention comprises recombinant DNA coding for an insecticidally-active form of the *Bacillus thuringiensis* endotoxin which is derived from a 6.6-type endotoxin gene carried on a plasmid harboured by strain A20. The maximum molecular weight of such endotoxins is about 103,000 Dalton.

We have made such recombinant DNA comprising the first 2910 basepairs (970 amino acid codons) of the N-terminal coding region of a plasmid-derived 6.6-type endotoxin gene from Strain A20. The 6.6-type construct we have made encodes a fusion protein that includes 28 amino acid codons derived from the pUC19 vector DNA. The *Bacillus thuringiensis*-derived portion of the recombinant DNA has 10 basepair changes as compared with the analogous plasmid-derived 6.6-type gene from *Bacillus thuringiensis* strain HD 73 (Adang et al, Gene 36, 1985, 289-300). Surprisingly, all of the base changes occur within the generally conserved N-terminal portion of the gene previously designated as a "highly-conserved" region (Whiteley and Schnepf, Ann. Rev. Microbiol., 40, 1986, pp549-576). Nine of the ten changes are clustered in a 0.35 kilobase segment which does not overlap with any of the 5 regions shown to be conserved in all types of endotoxin genes analysed to date (Sanchis et al., Molecular Microbiol., 3, 1989, pp229-238). Four of the 10 base changes result in amino acid substitutions.

The invention further comprises recombinant DNA coding for an insecticidally-active form of the *Bacillus thuringiensis* endotoxin which is derived from a 5.3-type endotoxin gene carried on a plasmid harboured by strain A20. The maximum molecular weight of the endotoxin is about 78,000 Daltons.

We have made such recombinant DNA comprising the first 2161 basepairs (696 amino acid codons) of the N-terminal coding region of a plasmid-derived 5.3-type endotoxin gene from Strain A20. This endotoxin gene differs from the analogous plasmid-derived 5.3-type gene from *Bacillus thuringiensis* strain HD-1 (Geiser etal., Gene 48, 1986, pp109-118) in that a deoxyguanosine base present in the published sequence at nucleotide 2024 is not present, resulting in a reading frame shift relative to the published structural gene. This frame shift results in a termination of the endotoxin gene product at amino acid residue 696, within the *Bacillus thuringiensis*-derived portion of the recombinant DNA. The recombinant DNA, however, encodes an insecticidally-active 5.3 type endotoxin protein.

In a further aspect, our invention comprises recombinant DNA coding for an insecticidally-active *Bacillus thuringiensis* endotoxin which is a chimera derived from sequences from at least two separate *Bacillus thuringiensis* genes. The molecular weight of the chimera may be of the order of 110,000 Daltons. Preferably the link or links between the sequences fall outside the hypervariable regions of such genes. In a more specific aspect, our invention comprises recombinant DNA coding for an insecticidally-active form of the *Bacillus thuringiensis* endotoxin comprising the first 1692 basepairs (564 amino acid codons) of the amino-terminal coding region from a 5.3-type endotoxin gene derived from Strain A20 and a restriction endonuclease Hind III-generated internal fragment of 1131 basepairs (377 amino acid codons) from a 4.5-type endotoxin gene derived from strain A20.

This chimetic gene encodes a novel fusion protein which also includes 28 amino acid codons derived from the pUC19 vector DNA. The *Bacillus thuringiensis* portion of the recombinant DNA has 97.1% DNA sequence homology with the 5.3-type gene from which it was largely derived. The internal Hind III-generated fragment used in the chimera and derived from the 4.5-type gene only differs from the analogous Hind III fragment from the 5.3-type gene by a 78 basepair insertion and 7 other physically separate base changes. These differences result in the in-frame addition of 26 amino acids due to the insertion, and in seven other amino acid changes; thus the novel protein has 91% amino acid homology with the 5.3-type gene product.

Recombinant genes according to our invention encoding insecticidally-active endotoxins may be of varying lengths. When cloning DNA from the A20 strain chromosome, it is convenient to use bacteriophage λ vectors or other cloning vectors that sequester the recombinant DNA from host cell enzymes that might cause homologous recombination.

Three *Escherichia coli* strains containing the cloned 6.6- and 5.3-type endotoxin genes from A20 and the chimetic endotoxin gene have been deposited at the National Collection of Industrial and Marine Bacteria at Aberdeen, Scotland. These are:

| Strain designation | Endotoxin Protein | NCIMB Accession No. |
|---|---|---|
| *E. coli* MC1022/pJH1 | 5.3-type fusion protein | 40049 |

| Strain designation | Endotoxin Protein | NCIMB Accession No. |
|---|---|---|
| E. coli MC1022/pJH2 | Novel chimeric molecule | 40050 |
| E. coli MC1022/pJH10 | 6.6-type fusion protein | 40211 |

The first two deposits were made on 23 Sep. 1988 and the third on 15 Sep. 1989.

The invention may be further understood by reference to the drawings, in which:

FIGS. 1A, 1B and 1C show diagramatically the structure of 6.6, 5.3 and chimetic-type genes, respectively as cloned;

Figure 2:
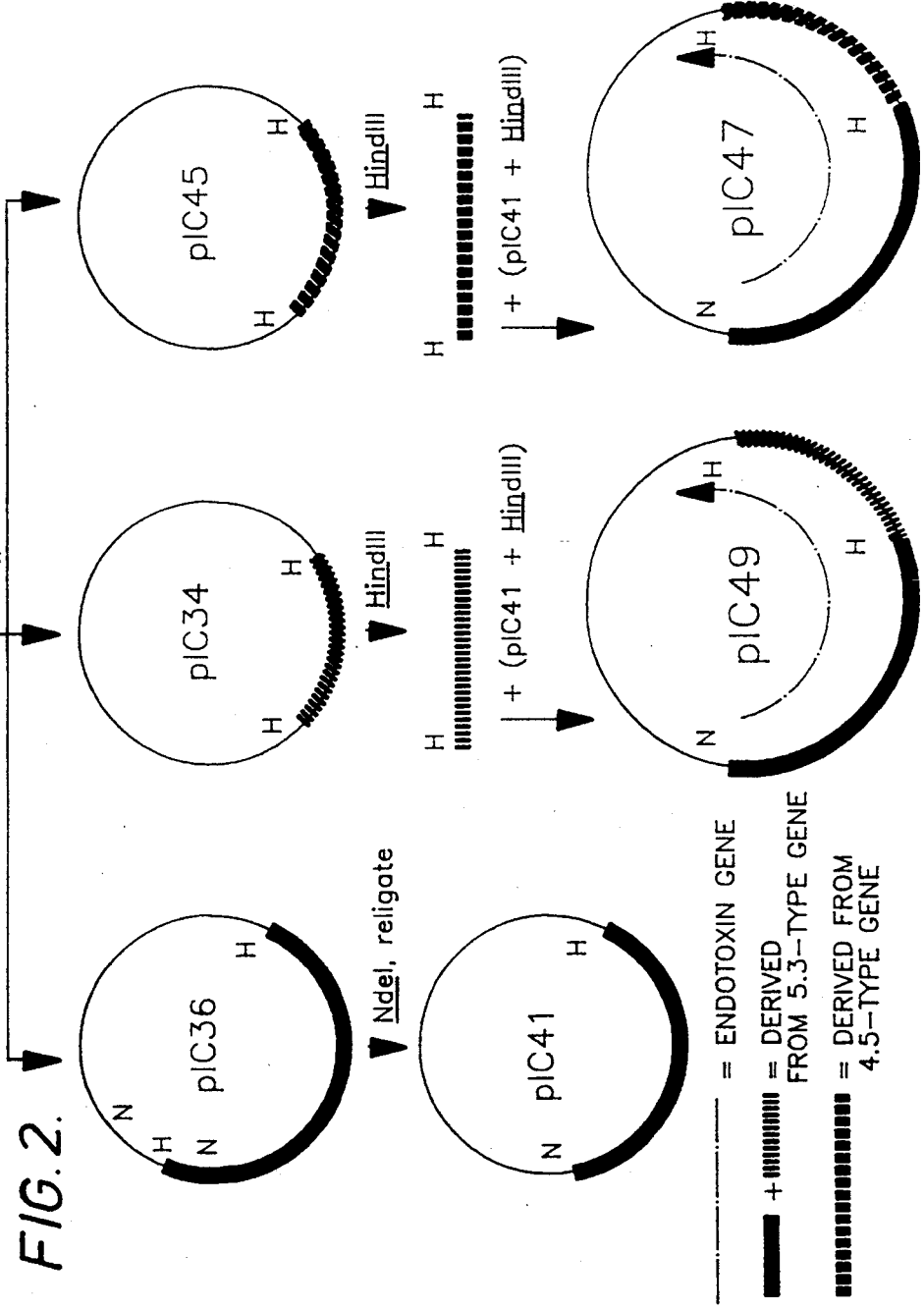
FIG. 2 illustrates schematically the construction of pJH1 (=pIC49), pJH2(=pIC47) from publicly available vector pUC19 and DNA obtained from A20 (NCIMB 12570)

FIGS. 3A1, 3A2, 3A3, 3B1, 3B2, 3B3, 4A1, 4A2, 4A3, 4B1, 4B2, 4B3, 5A1, 5A2, 5A3, 5B1, 5B2 and 5B3 show the base sequence, the amino acid sequence and the main restriction sites of the pJH10 endotoxin gene;

FIGS. 6A1, 6A2, 6A3, 6B1, 6B2, 6B3, 7A1, 7A2, 7A3, 7B1, 7B2, 7B3, 8A1, 8A2, 8A3, 8B1 and 8B2 show the base sequence, the amino acid sequence and the main restriction sites of the pJH1 endotoxin gene;

FIGS. 9A1, 9A2, 9B1, 9B2, 10A1, 10A2, 10B1, 10B2, 11A1, 11A2, 11B1, 11B2, 12A1 and 12A2 show the base sequence, the amino acid sequence and the main restriction sites of the chimetic pJH2 endotoxin gene;

FIG. 13 shows the characteristics of the pJH10 endotoxin gene product;

FIG. 14 shows the characteristics of the pJH1 endotoxin gene product;

FIG. 15 shows the characteristics of the pJH2 endotoxin gene product.

With further reference to FIG. 1, in this diagram H represents HindIII, D=DraI, X=XmnI, C= ClaI, E=EcoR1, R=EcoRV, P=Ps+I, B=BclI and K =KpnI. A dot shows a base change, while x indicates a base change and amino acid substitution in the 6.6-type gene of the invention as compared with the 6.6-type gene of strain HD73. The line under the 6.6-type gene indicates the 2.2 kilobase DraI fragment sequenced, while the line under the 5.3-type gene indicates the approximate length of the coding sequence. The heavy broken line indicates vector DNA. In FIG. 2, H is again HindIII, while N represents NdeI.

With reference to FIGS. 5A1, 5A2, 5A3, 5B1, 5B2 and 5B3, it should be noted that the sequence from nucleotide 2228 to nucleotide 2907 (internal DraI to HindIII) has been taken from the published literature. All other sequence data given for constructs of the inventions has been obtained independently by us.

In Heliothis virescens bioassays the chimetic gene product is of comparable potency to that of the 5.3-type gene over the normal bioassay time-course of six days.

The preferred method of producing recombinant DNA according to the invention is by culturing a sample of deposited strains NCIMB 40049, 40050 or 40211, obtainable from the National Collection of Industrial and Marine Bacteria, under suitable conditions in appropriate media. Such conditions and media are well-known to the art. Variant forms of DNA according to the invention may be made by cloning suitable DNA sequences from bacteria of strain A20 (also deposited at the NCIMB, under No 12570).

The invention further comprises insecticidal compositions comprising Bacillus thuringiensis endotoxin produced by expression of recombinant DNA according to the invention: as well as a process of combating insects which comprises exposing them to effective amounts of such endotoxin.

Insecticidal compositions according to the invention may be obtained from cultured cell suspensions by appropriate lysis techniques. Preparations of lysed cells (i.e. cell extracts) may be used directly, or concentrated by lyophilisation, followed by reconstitution.

The process of the invention is generally carried out by incorporation of the nonviable cell extracts into, or onto, the insect food source. Alternatively the novel insecticidal gene can be introduced into the genome of food plants normally attacked by Lepidopteran pests. For this purpose suitable plant regulatory DNA sequences are inserted adjacent the recombinant DNA in operative relation therewith so as to allow expression of the endotoxin in the plant. Specific examples of commercially important plants to be protected in this manner are maize, cotton, and tobacco. Various plant transformation methods are known to the art, for example the use of Ti plasmid vectors (for dicots) protoplast regeneration, embryo microinjection and microprojectiles.

Insects which are combated by the invention include various Lepidopteran pests, for example, those in Table 1.

TABLE 1

| COMMON NAME | LATIN NAME |
|---|---|
| European Corn Borer | Ostrinia nubilalis |
| Tobacco Budworm | Heliothis virescens |
| Tobacco Hornworm | Manduca sexta |
| Corn Earworm | Heliothis zea |
| Beet Armyworm | Spodoptera exigua |
| Fall Armyworm | Spodoptera frugiperda |
| Diamondback Moth | Plutella xylostella |
| Cabbage Looper | Trichoplusia ni |
| Eastern Spruce Budworm | Choristoneura fumiferana |
| Gypsy Moth | Lymantria dispar |

The following Examples illustrate the invention.

EXAMPLE 1

Cloning of the plasmid-derived 6.6-type endotoxin gene carried on pJH10 and of chromosomally-derived endotoxin genes.

Covalently-closed circular (ccc) plasmid DNA was prepared from Bacillus thuringiensis Strain A20 (NCIMB 12570) by techniques well-known in the art. Large molecular weight (greater than 40 kilobases) plasmid ccc DNA was isolated by size fractionation on 10%–40% sucrose step gradients prior to digestion with restriction endonuclease Hind III and ligation into the Hind III—digested plasmid vector pUC19. The ligation reacted mixture was transformed into E. coli Strain MC1022, an ampicillin-sensitive strain with the genotype ara D139, Δ(ara, leu) 7697, Δ(lac Z) M15, gal U, gal K, str A. Amipicillin-resistant transformed colonies containing the 6.6 kilobase Hind III fragment were detected by hybridisation of lysed colonies fixed to nitrocellulose using a radioactively-labelled fragment of the Strain HD73 6.6-type endotoxin gene as a probe. Isolate pJH10 was further characterised by DNA hybridisation, restriction endonuclease mapping, and DNA sequence analysis techniques, all of which are well known in the art.

Endotoxin genes were cloned from chromosomal DNA prepared from Strain A20 (NCIMB 12570) as follows:

A 500 ml culture of Strain A20 was grown in L-broth at 37° C., with shaking, until an $O.D._{600}=1.00$. Cells were harvested by centrifugation at 8000 rounds per minute (rpm) for 10 minutes at 4° C., then re-suspended in 5 ml TES buffer (50 mM TriS-HCl pH7.5, 50mM NaCl, 5 mM EDTA). Cells were treated for 30 minutes at 37° C. with lysozyme (0.5 mg/ml final concentration) and RNase (0.1 mg/ml final concentration taken from a stock solution of 5 mg/ml boiled at 100° C for 5 minutes prior to use). Lysis was completed by the addition of Sarcosyl to give a final concentration of 0.8% and incubation at 37° C. for 60 minutes in the presence of Pronase (0.5mg/ml final concentration taken from a stock solution of 5 mg/ml pre-incubated at 37° C. for 60 minutes prior to use). Lysate volume was adjusted to 9.0 ml in the 50 mM Tris-HCl pH 7.6, 10 mM EDTA, prior to the addition of 9.2 g caesium chloride (CsCl). After the CsCl dissolved, 1.25 ml of a 5 mg/ml solution of ethidium bromide was added prior to isopyonic centrifugation of the mixture at 40,000 rpm for 48 hours at 15° C.

After removal of CsCl and ethidium bromide by conventional techniques, an aliquot of purified chromosomal DNA was partially digested with the restriction endonuclease EcoR1 prior to ligation into EcoR1-digested bacteriophage λ EMBL4 vector DNA. Ligation reaction mixtures were packaged into viable phage particles using a commercially-available kit from Amersham International PLC. The resultant recombinant phage particles were selected by growth on *E. coli* host strain PE392, a P2 lysogen of strain LE392 which has the genotype hsd R514 ($r_k-$, $M_k+$), sup E44, SUP F58, lacY1 or Δ(lac12Y), gal K2, gal T22, met B1, trp55. Recombinant phage carrying one or more endotoxin genes were detected by hybridisation of lysed plaques fixed to nitrocellulose using a radiolabelled fragment of the Strain A20 6.6-type plasmid-derived endotoxin gene as a probe.

Plaques containing endotoxin genes were purified and characterised by restriction endonuclease mapping techniques well known in the art.

EXAMPLE 2

Construction of plasmid pJH2 containing the chimeric endotoxin gene.

DNA was prepared from plasmids pIC41 and pIC45, the derivation of which is shown in FIG. 2. pIC41 DNA was digested with restriction endonuclease HindIII and joined to the isolated, internal 1131 basepair HindIII-generated fragment from plasmid pIC45 using T4 DNA ligase. Methods for DNA preparation, DNA fragment purification and in vitro ligation reactions are all well known to the art. The ligation reaction mixture was introduced by transformation into *E. coli* strain MC1022, an F- strain with the genotype ara D139, Δ(ara, leu) 7697, Δ(lacZ) M15, galU, gal, str A. Ampicillin-resistant transformed colonies containing the 1131 basepair fragment were detected by hybridisation of lysed colonies fixed to nitrocellulose filters using the radioactively labelled 1131 basepair fragment as a probe. DNA samples from colonies reacting to the probe were checked for the presence of the introduced 1131 basepair fragment in the correct orientation. Transformation of *E.coli* cells made competent by treatment with calcium chloride, colony blotting, nick-translation of DNA to prepare radioactive probes, DNA hybridisation techniques, and restriction endonuclease "mapping" techniques are all well known in the art.

pJH1 was made in a similar manner from pIC34 and pIC41, as shown in FIG. 2.

EXAMPLE 3

Preparation of insecticidal extracts according to the invention.

*E.coli* strain MC1022/pIC47 was grown in 400 ml Luria-broth supplemented with 50 μg Ampicillin per ml overnight at 37 C. with shaking. Cells were harvested by centrifugation at 8000 rpm for 10 minutes at 4 C. and resuspended in 26.4 ml lysing buffer (150 mM NaCl, 20 mM Tris pH 8, 5 mM EDTA, 7 mM β-mercaptoethanol). The resuspended cells were placed on ice and then 0.3 ml 0.1M phenylmethylsulphonylfluoride (PMSF) was added, followed by 3 ml of a freshly prepared solution of 10 mg lysozyme per ml, followed by a further addition of 0.3 ml PMSF. The mixture was left for 30 minutes on ice. The cell suspension was subjected to sonic disruption by treatment for 45 seconds with a one centimeter diameter sonicator probe operated at a frequency of 12 microns on an MSE Soniprep 150 sonifier. The sonicated sample was then centrifuged at 11000 rpm for 20 minutes at 4° C. (using 50 cc capacity sterile centrifuge tubes). The supernatant was recovered by pouring off into a clean, sterile plastic container then dialyzed overnight at 4° C. in 20 mM phosphate buffer (mono- and di-basic) pH 7.2. Insecticidal extracts can be stored frozen, or lyophilised and stored frozen.

EXAMPLE 4

Efficacy of insecticidal extracts prepared from *E.coli* strains MC1022/pJH1 and MC1022/pJH2 in controlling *Heliothis virescens* and MC1022/pJH10 in controlling *Heliothis virescens* and *Ostrinia nubilalis*.

Insecticidal extract was added to molten insect diet (e.g. standard Heliothis diet) to give a final concentration of, for example, 1 ml per 10 g of diet (equivalent to approximately 510 ppm freeze-dried extract per treatment). 2.5 ml of treated diet was added to each of 10 plastic pots, covered and allowed to solidify. One first-instar larva was added to each pot and incubated at 27° C. for six days, at which time the results were recorded. In tests with lower treatment concentrations (e.g. 0.1 ml extract per 10 g of diet), surviving larvae at six days were left for longer periods of observation to allow documentation of altered stability. Results of typical experiments are shown in Tables 2 and 3.

EXAMPLE 5

Efficacy of insecticidal extracts prepared from strains MC1022/pJH2 and pJH1 on Lepidopteran larvae.

Lyophilised extracts from *E.coli* strains MC1022/pJB2 and MC1022/pdH1 were reconstituted in distilled water to give a stock solution which was then added, in varying amounts, to molten diet as described above in Example 4. Results of a typical bioassay experiment on *Plutella xylostella* (Diamondback moth, DBM), *Heliothis zea* (Corn earworm, CEW) and *Trichoplusia ni* (Cabbage looper, CL) are given in Table 4.

The work described herein was all done in conformity with physical and biological containment requirements specified in the NIH and GMAC guidelines.

TABLE 2

Bioassay Results 6 Days After Treatment

Inhibition of Development

| Construct | Plasmid | Percent Mortality | Larval Instar: 1 | 2E | 2L | 3E | 3L | 4 |
|---|---|---|---|---|---|---|---|---|
| Untreated controls | — | 0 | 5 | 2 | 8 | 4 | 1 | — |
| | | 5 | — | — | 3 | 4 | 4 | 5 |
| Vector control | pUC19 | 0 | — | 4 | 3 | 3 | — | — |
| | | 0 | — | 2 | — | 4 | 2 | 2 |
| Positive control | pIC18* | 100 | — | — | — | — | — | — |
| | | 80 | 2 | — | — | — | — | — |
| 5.3-type endotoxin | pJH1 | 90 | 1 | — | — | — | — | — |
| Chimeric endotoxin | pJH2 | 90 | 1 | — | — | — | — | — |

*carries an endotoxin gene from *B. thuringiensis* HD73
E = early
L = late

TABLE 3

Heliothis virescens and Ostrinia nubilalis Bioassay Results Six Days after Treatment

| | | H. virescens | | O. nubilalis | |
|---|---|---|---|---|---|
| GENE TYPE | PLASMID | PERCENT MORTALITY | LARVAL SIZE* | PERCENT MORTALITY | LARVAL SIZE* |
| Untreated Controls | — | 0 | 2nd-4th instar | 0 | 6.2 mm |
| Vector Control | pUC19 | 0 | 2nd-3rd instar | 5 | 5.7 mm |
| Positive Control+ | pIC18* | 30 | 1st instar | 50 | 2.0 mm |
| 6.6 Type Gene | pJH10 | 50 | 1st instar | 40 | 2.0 mm |

*Developmental stage or length of surviving larvae
+Carries a 6.5-type endotoxin gene from *B. thuringiensis* strain HD73

TABLE 4

| | | % Mortality | | | % Stunting | | |
|---|---|---|---|---|---|---|---|
| Construct | Plasmid | DBM | CEW | CL | DBM | CEW | CL |
| Untreated control | — | 0 | 0 | 0 | 0 | 0 | 0 |
| Vector control | pUC19 | 0 | 0 | 0 | 0 | 0 | 0 |
| Positive control | pIC18 | 100 | 5 | 0 | 0 | 95 | 100 |
| 5.3-type endotoxin | pJH1 | 95 | 0 | 0 | 5 | 100 | 45 |
| Chimeric endotoxin | pJH2 | 100 | 5 | 0 | 0 | 95 | 65 |

DEPOSIT OF MICROORGANISMS

The specification refers to four microorganisms that have been deposited. These are shown below. All four were deposited at the National Collections of Industrial and Marine Bacterial Limited (NCIMB) of PO BOX 31, 135 Abbey Road, Aberdeen, AB9 8DG, Scotland.

| Strain designation | Date of Deposit | NCIMB Accession No. |
|---|---|---|
| *Bacillus thuringiensis kurstaki* A20 | 20 Oct 1987 | 12570 |
| *E. coli* MC1022/pJH1 | 23 Sep 1988 | 40049 |
| *E. coli* MC1022/pJH2 | 23 Sep 1988 | 40050 |
| *E. coli* MC1022/pJH10 | 15 Sep 1989 | 40211 |

The *Bacillus thuringiensis* strain A20 is fully described in our European Patent Publication no 325037, the disclosure of which is incorporated herein by reference. The three *E. coli* strains are of well known type, differing only in the plasmids they carry, full details of which are given elsewhere in the present specification.

We claim:

1. Recombinant DNA coding for an insecticidally active form of the *Bacillus thuringiensis* endotoxin comprising DNA derived from a 6.6-type endotoxin gene of the A20 strain of *Bacillus thuringiensis*.

2. Recombinant DNA as claimed in claim 1 wherein the DNA is chromosomally derived.

3. Recombinant DNA as claimed in claim 1 comprising the first 2910 basepairs (970 amino acid codons) of the N-terminal coding region of a plasmid-derived 6.6-type endotoxin gene from Strain A20.

4. Recombinant DNA as claimed in claim 3 which is derived from the *E. coli* strain deposited at the NCIMB under the number 40211.

5. Recombinant DNA coding for an insecticidally-active form of the *Bacillus thuringiensis* endotoxin comprising the first 1692 basepairs (564 amino acid codons) of the amino-terminal coding region from a 5.3-type endotoxin gene derived from Strain A20 and a restriction endonuclease Hind III-generated internal fragment of 1131 basepairs (377 amino acid codons) from a 4.5-type endotoxin gene derived from strain A20.

6. Recombinant DNA as claimed in claim 5 which is derived from the *E. coli* strain deposited at the NCIMB under the number 40050.

7. Recombinant DNA as claimed in claim 1 or claim 5 comprising a transcriptional initiation region operative in plants and positioned for transcription of the DNA coding for the *Bacillus thuringiensis* endotoxin.

( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 2990 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| TATGTTTTAA | ATTGTAGTAA | TGAAAAACAG | TATTATATCA | TAATGAATTG | GTATCTTAAT | 60 |
| AAAAGAGATG | GAGGTAACTT | ATGGATAACA | ATCCGAACAT | CAATGAATGC | ATTCCTTATA | 120 |
| ATTGTTTAAG | TAACCCTGAA | GTAGAAGTAT | TAGGTGGAGA | AAGAATAGAA | ACTGGTTACA | 180 |
| CCCCAATCGA | TATTTCCTTG | TCGCTAACGC | AATTTCTTTT | GAGTGAATTT | GTTCCCGGTG | 240 |
| CTGGATTTGT | GTTAGGACTA | GTTGATATAA | TATGGGGAAT | TTTTGGTCCC | TCTCAATGGG | 300 |
| ACGCATTTCT | TGTACAAATT | GAACAGTTAA | TTAACCAAAG | AATAGAAGAA | TTCGCTAGGA | 360 |
| ACCAAGCCAT | TTCTAGATTA | GAAGGACTAA | GCAATCTTTA | TCAAATTTAC | GCAGAATCTT | 420 |
| TTAGAGAGTG | GGAAGCAGAT | CCTACTAATC | CAGCATTAAG | AGAAGAGATG | CGTATTCAAT | 480 |
| TCAATGACAT | GAACAGTGCC | CTTACAACCG | CTATTCCTCT | TTTGGCAGTT | CAAAATTATC | 540 |
| AAGTTCCTCT | TTTATCAGTA | TATGTTCAAG | CTGCAAATTT | ACATTTATCA | GTTTGAGAG | 600 |
| ATGTTTCAGT | GTTTGGACAA | AGGTGGGGAT | TTGATGCCGC | GACTATCAAT | AGTCGTTATA | 660 |
| ATGATTTAAC | TAGGCTTATT | GGCAACTATA | CAGATTATGC | TGTACGCTGG | TACAATACGG | 720 |
| GATTAGAACG | TGTATGGGGA | CCGGATTCTA | GAGATTGGGT | AAGGTATAAT | CAATTTAGAA | 780 |
| GAGAATTAAC | ACTAACTGTA | TTAGATATCG | TTGCTCTGTT | CCCGAATTAT | GATAGTAGAA | 840 |
| GATATCCAAT | TCGAACAGTT | TCCCAATTAA | CAAGAGAAAT | TTATACAAAC | CCAGTATTAG | 900 |
| AAAATTTTGA | TGGTAGTTTT | CGAGGCTCGG | CTCAGGGCAT | AGAAAGAAGT | ATTAGGAGTC | 960 |
| CACATTTGAT | GGATATACTT | AACAGTATAA | CCATCTATAC | GGATGCTCAT | AGGGGTTATT | 1020 |
| ATTATTGGTC | AGGGCATCAA | ATAATGGCTT | CTCCTGTCGG | GTTTTCGGGG | CCAGAATTCA | 1080 |
| CGTTTCCGCT | ATATGGAACC | ATGGGAAATG | CAGCTCCACA | ACAACGTATT | GTTGCTCAAC | 1140 |
| TAGGTCAGGG | CGTGTATAGA | ACATTATCCT | CTACTTTTTA | TAGAAGACCT | TTTAATATAG | 1200 |
| GGATAAATAA | TCAACAACTA | TCTGTTCTTG | ACGGGACAGA | ATTTGCTTAT | GGAACCTCCT | 1260 |
| CAAATTTGCC | ATCCGCTGTA | TACAGAAAAA | GCGGAACGGT | AGATTCGCTG | GATGAAATAC | 1320 |
| CACCACAGAA | TAACAACGTG | CCACCTAGGC | AAGGATTTAG | TCATCGATTA | AGCCATGTTT | 1380 |
| CAATGTTTCG | TTCAGGCTCT | AGTAGTAGTG | TAAGTATAAT | AAGAGCTCCT | ATGTTCTCTT | 1440 |
| GGATACATCG | TAGTGCTGAA | TTTAATAATA | TAATTGCATC | GGATAGTATT | ACTCAAATCC | 1500 |
| CTGCAGTGAA | GGGAAACTTT | CTTTTTAATG | GTTCTGTAAT | TTCAGGACCA | GGATTTACTG | 1560 |
| GTGGGGACTT | AGTTAGATTA | AATAGTAGTG | GAAATAACAT | TCAGAATAGA | GGGTATATTG | 1620 |
| AAGTTCCAAT | TCACTTCCCA | TCGACATCTA | CCAGATATCG | AGTTCGTGTA | CGGTATGCTT | 1680 |
| CTGTAACCCC | GATTCACCTC | AACGTTAATT | GGGGTAATTC | ATCCATTTTT | TCCAATACAG | 1740 |
| TACCAGCTAC | AGCTACGTCA | TTAGATAATC | TACAATCAAG | TGATTTTGGT | TATTTTGAAA | 1800 |
| GTGCCAATGC | TTTTACATCT | TCATTAGGTA | ATATAGTAGG | TGTTAGAAAT | TTTAGTGGGA | 1860 |
| CTGCAGGAGT | GATAATAGAC | AGATTTGAAT | TTATTCCAGT | TACTGCAACA | CTCGAGGCTG | 1920 |
| AATATAATCT | GGAAAGAGCG | CAGAAGGCGG | TGAATGCGCT | GTTTACGTCT | ACAAACCAAC | 1980 |

| | | | | | | |
|---|---|---|---|---|---|---|
| TAGGGCTAAA | AACAAATGTA | ACGGATTATC | ATATTGATCA | AGTGTCCAAT | TTAGTTACGT | 2040 |
| ATTTATCGGA | TGAATTTTGT | CTGGATGAAA | AGCGAGAATT | GTCCGAGAAA | GTCAAACATG | 2100 |
| CGAAGCGACT | CAGTGATGAA | CGCAATTTAC | TCCAAGATTC | AAATTTCAAA | GACATTAATA | 2160 |
| GGCAACCAGA | ACGTGGGTGG | GGCGGAAGTA | CAGGGATTAC | CATCCAAGGA | GGGGATGACG | 2220 |
| TATTTAAAGA | AAATTACGTC | ACACTATCAG | GTACCTTTGA | TGAGTGCTAT | CCAACATATT | 2280 |
| TGTATCAAAA | AATCGATGAA | TCAAAATTAA | AAGCCTTTAC | CCGTTATCAA | TTAAGAGGGT | 2340 |
| ATATCGAAGA | TAGTCAAGAC | TTAGAAATCT | ATTTAATTCG | CTACAATGCA | AAACATGAAA | 2400 |
| CAGTAAATGT | GCCAGGTACG | GGTTCCTTAT | GGCCGCTTTC | AGCCCAAAGT | CCAATCGGAA | 2460 |
| AGTGTGGAGA | GCCGAATCGA | TGCGCGCCAC | ACCTTGAATG | GAATCCTGAC | TTAGATTGTT | 2520 |
| CGTGTAGGGA | TGGAGAAAAG | TGTGCCCATC | ATTCGCATCA | TTTCTCCTTA | GACATTGATG | 2580 |
| TAGGATGTAC | AGACTTAAAT | GAGGACCTAG | GTGTATGGGT | GATCTTTAAG | ATTAAGACGC | 2640 |
| AAGATGGGCA | CGCAAGACTA | GGGAATCTAG | AGTTTCTCGA | AGAGAAACCA | TTAGTAGGAG | 2700 |
| AAGCGCTAGC | TCGTGTGAAA | AGAGCGGAGA | AAAATGGAG | AGACAAACGT | GAAAAATTGG | 2760 |
| AATGGGAAAC | AAATATCGTT | TATAAGAGG | CAAAAGAATC | TGTAGATGCT | TTATTTGTAA | 2820 |
| ACTCTCAATA | TGATCAATTA | CAAGCGGATA | CGAATATTGC | CATGATTCAT | GCGGCAGATA | 2880 |
| AACGTGTTCA | TAGCATTCGA | GAAGCTTGGC | GTAATCATGG | TCATAGCTGT | TTCCTGTGTG | 2940 |
| AAATTGTTAT | CCGCTCACAA | TTCCACACAA | CATACGAGCC | GGAAGCATAA | | 2990 |

( 2 ) INFORMATION FOR SEQ ID NO:2:

( i ) SEQUENCE CHARACTERISTICS:
        ( A ) LENGTH: 2815 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| AAATTGTAGT | AATGAAAAAC | AGTATTATAT | CATAATGAAT | TGGTATCTTA | ATAAAAGAGA | 60 |
| TGGAGGTAAC | TTATGGATAA | CAATCCGAAC | ATCAATGAAT | GCATTCCTTA | TAATTGTTTA | 120 |
| AGTAACCCTG | AAGTAGAAGT | ATTAGGTGGA | GAAAGAATAG | AAACTGGTTA | CACCCCAATC | 180 |
| GATATTTCCT | TGTCGCTAAC | GCAATTTCTT | TTGAGTGAAT | TTGTTCCCGG | TGCTGGATTT | 240 |
| GTGTTAGGAC | TAGTTGATAT | AATATGGGGA | ATTTTTGGTC | CCTCTCAATG | GGACGCATTT | 300 |
| CTTGTACAAA | TTGAACAGTT | AATTAACCAA | AGAATAGAAG | AATTCGCTAG | GAACCAAGCC | 360 |
| ATTTCTAGAT | TAGAAGGACT | AAGCAATCTT | TATCAAATTT | ACGCAGAATC | TTTTAGAGAG | 420 |
| TGGGAAGCAG | ATCCTACTAA | TCCAGCATTA | AGAGAAGAGA | TGCGTATTCA | ATTCAATGAC | 480 |
| ATGAACAGTG | CCCTTACAAC | CGCTATTCCT | CTTTTTGCAG | TTCAAAATTA | TCAAGTTCCT | 540 |
| CTTTTATCAG | TATATGTTCA | AGCTGCAAAT | TTACATTTAT | CAGTTTTGAG | AGATGTTTCA | 600 |
| GTGTTTGGAC | AAAGGTGGGG | ATTTGATGCC | GCGACTATCA | ATAGTCGTTA | TAATGATTTA | 660 |
| ACTAGGCTTA | TTGGCAACTA | TACAGATCAT | GCTGTACGCT | GGTACAATAC | GGGATTAGAG | 720 |
| CGTGTATGGG | GACCGGATTC | TAGAGATTGG | ATAAGATATA | ATCAATTTAG | AAGAGAATTA | 780 |
| ACACTAACTG | TATTAGATAT | CGTTTCTCTA | TTTCCGAACT | ATGATAGTAG | AACGTATCCA | 840 |
| ATTCGAACAG | TTTCCCAATT | AACAAGAGAA | ATTTATACAA | ACCCAGTATT | AGAAAATTTT | 900 |
| GATGGTAGTT | TTCGAGGCTC | GGCTCAGGGC | ATAGAAGGAA | GTATTAGGAG | TCCACATTTG | 960 |
| ATGGATATAC | TTAACAGTAT | AACCATCTAT | ACGGATGCTC | ATAGAGGAGA | ATATTATTGG | 1020 |

| | | | | | |
|---|---|---|---|---|---|
| TCAGGGCATC | AAATAATGGC | TTCTCCTGTA | GGGTTTTCGG | GGCCAGAATT | CACTTTTCCG | 1080 |
| CTATATGGAA | CTATGGGAAA | TGCAGCTCCA | CAACAACGTA | TTGTTGCTCA | ACTAGGTCAG | 1140 |
| GGCGTGTATA | GAACATTATC | GTCCACTTTA | TATAGAAGAC | CTTTTAATAT | AGGGATAAAT | 1200 |
| AATCAACAAC | TATCTGTTCT | TGACGGGACA | GAATTTGCTT | ATGGAACCTC | CTCAAATTTG | 1260 |
| CCATCCGCTG | TATACAGAAA | AAGCGGAACG | GTAGATTCGC | TGGATGAAAT | ACCGCCACAG | 1320 |
| AATAACAACG | TGCCACCTAG | GCAAGGATTT | AGTCATCGAT | TAAGCCATGT | TTCAATGTTT | 1380 |
| CGTTCAGGCT | TTAGTAATAG | TAGTGTAAGT | ATAATAAGAG | CTCCTATGTT | CTCTTGGATA | 1440 |
| CATCGTAGTG | CTGAATTTAA | TAATATAATT | CCTTCATCAC | AAATTACACA | AATACCTTTA | 1500 |
| ACAAAATCTA | CTAATCTTGG | CTCTGGAACT | TCTGTCGTTA | AAGGACCAGG | ATTTACAGGA | 1560 |
| GGAGATATTC | TTCGAAGAAC | TTCACCTGGC | CAGATTTCAA | CCTTAAGAGT | AAATATTACT | 1620 |
| GCACCATTAT | CACAAAGATA | TCGGGTAAGA | ATTCGCTACG | CTTCTACCAC | AAATTTACAA | 1680 |
| TTCCATACAT | CAATTGACGG | AAGACCTATT | AATCAGGGA | ATTTTCAGC | AACTATGAGT | 1740 |
| AGTGGGAGTA | ATTTACAGTC | CGGAAGCTTT | AGGACTGTAG | GTTTTACTAC | TCCGTTTAAC | 1800 |
| TTTTCAAATG | GATCAAGTGT | ATTTACGTTA | AGTGCTCATG | TCTTCAATTC | AGGCAATGAA | 1860 |
| GTTTATATAG | ATCGAATTGA | ATTGTTCCG | GCAGAAGTAA | CCTTTGAGGC | AGAATATGAT | 1920 |
| TTAGAAAGAG | CACAAAAGGC | GGTGAATGAG | CTGTTTACTT | CTTCCAATCA | AATCGGGTTA | 1980 |
| AAAACAGATG | TGACGGATTA | TCATATTGAT | CAAGTATCCA | ATTTAGTTGA | GTGTTTATCT | 2040 |
| GATGAATTTT | GTCTGGATGA | AAAAAAAGAA | TTGTCCGAGA | AAGTCAAACA | TGCGAACGAC | 2100 |
| TTAGTGATGA | GCGGAATTTA | CTTCAAGATC | CAAACTTTAG | AGGGATCAAT | AGACAACTAG | 2160 |
| ACCGTGGCTG | GAGAGGAAGT | ACGGATATTA | CCATCCAAGG | AGGCGATGAC | GTATTCAAAG | 2220 |
| AGAATTACGT | TACGCTATTG | GGTACCTTTG | ATGAGTGCTA | TCCAACGTAT | TTATATCAAA | 2280 |
| AAATAGATGA | GTCGAAATTA | AAAGCCTATA | CCCGTTACCA | ATTAAGAGGG | TATATCGAAG | 2340 |
| ATAGTCAAGA | CTTAGAAATC | TATTTAATTC | GCTACAATGC | CAAACACGAA | ACAGTAAATG | 2400 |
| TGCCAGGTAC | GGGTTCCTTA | TGGCCGCTTT | CAGCCCCAAG | TCCAATCGGA | AAATGTGCCC | 2460 |
| ATCATTCCCA | TCATTTCTCC | TTGGACATTG | ATGTTGGATG | TACAGACTTA | AATGAGGACT | 2520 |
| TAGGTGTATG | GGTGATATTC | AAGATTAAGA | CGCAAGATGG | CCATGCAAGA | CTAGGAAATC | 2580 |
| TAGAATTTCT | CGAAGAGAAA | CCATTAGTAG | GAGAAGCACT | AGCTCGTGTG | AAAAGAGCGG | 2640 |
| AGAAAAAATG | GAGAGACAAA | CGTGAAAAAT | TGGAATGGGA | AACAAATATT | GTTTATAAAG | 2700 |
| AGGCAAAAGA | ATCTGTAGAT | GCTTTATTTG | TAAACTCTCA | ATATGATAGA | TTACAAGCGG | 2760 |
| ATACCAACAT | CGCGATGATT | CATGCGGCAG | ATAAACGCGT | TCATAGCATT | CGAGA | 2815 |

( 2 ) INFORMATION FOR SEQ ID NO:3:

( i ) SEQUENCE CHARACTERISTICS:
        ( A ) LENGTH: 3066 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
| GTTAACACCC | TGGGTCAAAA | ATTGATATTT | AGTAAAATTA | GTTGCACTTT | GTGCATTTTT | 60 |
| TCATAAGATG | AGTCATATGT | TTTAAATTGT | AGTAATGAAA | AACAGTATTA | TATCATAATG | 120 |
| AATTGGTATC | TTAATAAAAG | AGATGGAGGT | AACTTATGGA | TAACAATCCG | AACATCAATG | 180 |
| AATGCATTCC | TTATAATTGT | TTAAGTAACC | CTGAAGTAGA | AGTATTAGGT | GGAGAAAGAA | 240 |
| TAGAAACTGG | TTACACCCCA | ATCGATATTT | CCTTGTCGCT | AACGCAATTT | CTTTTGAGTG | 300 |

| | | | | | |
|---|---|---|---|---|---|
| AATTTGTTCC | CGGTGCTGGA | TTTGTGTTAG | GACTAGTTGA | TATAATATGG | GGAATTTTTG | 360 |
| GTCCCTCTCA | ATGGGACGCA | TTTCTTGTAC | AAATTGAACA | GTTAATTAAC | CAAAGAATAG | 420 |
| AAGAATTCGC | TAGGAACCAA | GCCATTTCTA | GATTAGAAGG | ACTAAGCAAT | CTTTATCAAA | 480 |
| TTTACGCAGA | ATCTTTTAGA | GAGTGGGAAG | CAGATCCTAC | TAATCCAGCA | TTAAGAGAAG | 540 |
| AGATGCGTAT | TCAATTCAAT | GACATGAACA | GTGCCCTTAC | AACCGCTATT | CCTCTTTTTG | 600 |
| CAGTTCAAAA | TTATCAAGTT | CCTCTTTTAT | CAGTATATGT | TCAAGCTGCA | AATTTACATT | 660 |
| TATCAGTTTT | GAGAGATGTT | TCAGTGTTTG | GACAAAGGTG | GGGATTTGAT | GCCGCGACTA | 720 |
| TCAATAGTCG | TTATAATGAT | TTAACTAGGC | TTATTGGCAA | CTATACAGAT | CATGCTGTAC | 780 |
| GCTGGTACAA | TACGGGATTA | GAGCGTGTAT | GGGGACCGGA | TTCTAGAGAT | TGGATAAGAT | 840 |
| ATAATCAATT | TAGAAGAGAA | TTAACACTAA | CTGTATTAGA | TATCGTTTCT | CTATTTCCGA | 900 |
| ACTATGATAG | TAGAACGTAT | CCAATTCGAA | CAGTTTCCCA | ATTAACAAGA | GAAATTTATA | 960 |
| CAAACCCAGT | ATTAGAAAAT | TTTGATGGTA | GTTTTCGAGG | CTCGGCTCAG | GGCATAGAAG | 1020 |
| GAAGTATTAG | GAGTCCACAT | TTGATGGATA | TACTTAACAG | TATAACCATC | TATACGGATG | 1080 |
| CTCATAGAGG | AGAATATTAT | TGGTCAGGGC | ATCAAATAAT | GGCTTCTCCT | GTAGGGTTTT | 1140 |
| CGGGGCCAGA | ATTCACTTTT | CCGCTATATG | GAACTATGGG | AAATGCAGCT | CCACAACAAC | 1200 |
| GTATTGTTGC | TCAACTAGGT | CAGGGCGTGT | ATAGAACATT | ATCGTCCACT | TTATATAGAA | 1260 |
| GACCTTTTAA | TATAGGGATA | AATAATCAAC | AACTATCTGT | TCTTGACGGG | ACAGAATTTG | 1320 |
| CTTATGGAAC | CTCCTCAAAT | TTGCCATCCG | CTGTATACAG | AAAAAGCGGA | ACGGTAGATT | 1380 |
| CGCTGGATGA | AATACCGCCA | CAGAATAACA | ACGTGCCACC | TAGGCAAGGA | TTTAGTCATC | 1440 |
| GATTAAGCCA | TGTTTCAATG | TTTCGTTCAG | GCTTAGTAA | TAGTAGTGTA | AGTATAATAA | 1500 |
| GAGCTCCTAT | GTTCTCTTGG | ATACATCGTA | GTGCTGAATT | TAATAATATA | ATTCCTTCAT | 1560 |
| CACAAATTAC | ACAAATACCT | TTAACAAAAT | CTACTAATCT | TGGCTCTGGA | ACTTCTGTCG | 1620 |
| TTAAAGGACC | AGGATTTACA | GGAGGAGATA | TTCTTCGAAG | AACTTCACCT | GGCCAGATTT | 1680 |
| CAACCTTAAG | AGTAAATATT | ACTGCACCAT | TATCACAAAG | ATATCGGGTA | AGAATTCGCT | 1740 |
| ACGCTTCTAC | CACAAATTTA | CAATTCCATA | CATCAATTGA | CGGAAGACCT | ATTAATCAGG | 1800 |
| GGAATTTTTC | AGCAACTATG | AGTAGTGGGA | GTAATTTACA | GTCCGGAAGC | TTTAGGACTG | 1860 |
| TAGGTTTTAC | TACTCCGTTT | AACTTTCAA | ATGGATCAAG | TGTATTTACG | TTAAGTGCTC | 1920 |
| ATGTCTTCAA | TTCAGGCAAT | GAAGTTTATA | TAGATCGAAT | TGAATTTGTT | CCGGCAGAAG | 1980 |
| TAACCTTTGA | GGCAGAATAT | GATTTAGAAA | GAGCACAAAA | GGCGGTGAAT | GAGCTGTTTA | 2040 |
| CTTCTTCCAA | TCAAATCGGG | TTAAAAACAG | ATGTGACGGA | TTATCATATT | GATCAAGTAT | 2100 |
| CCAATTTAGT | TGAGTGTTTA | TCAGATGAAT | TTTGTCTGGA | TGAAAAACAA | GAATTGTCCG | 2160 |
| AGAAAGTCAA | ACATGCGAAG | CGACTTAGTG | ATGAGCGGAA | TTTACTTCAA | GATCCAAACT | 2220 |
| TCAGAGGGAT | CAATAGACAA | CTAGACCGTG | GCTGGAGAGG | AAGTACGGAT | ATTACCATCC | 2280 |
| AAGGAGGCGA | TGACGTATTC | AAAGAGAATT | ACGTTACGCT | ATTGGGTACC | TTTGATGAGT | 2340 |
| GCTATCCAAC | GTATTTATAT | CAAAAAATAG | ATGAGTCGAA | ATTAAAGCC | TATACCCGTT | 2400 |
| ATCAATTAAG | AGGGTATATC | GAAGATAGTC | AAGACTTAGA | AATCTATTTA | ATTCGCTACA | 2460 |
| ATGCAAAACA | TGAAACAGTA | AATGTGCCAG | GTACGGGTTC | CTTATGGCCG | CTTTCAGCCC | 2520 |
| AAAGTCCAAT | CGGAAAGTGT | GGAGAGCCGA | ATCGATGCGC | GCCACACCTT | GAGTGGAATC | 2580 |
| CTGACTTAGA | TTGTTCGTGT | AGGGATGGAG | AAAAGTGTGC | CCATCATTCG | CATCATTTCT | 2640 |
| CCTTAGACAT | TGATGTAGGA | TGTACAGACT | TAAATGAGGA | CCTAGGTGTA | TGGGTGATCT | 2700 |
| TTAAGATTAA | GACGCAAGAT | GGGCACGCAA | GACTAGGGAA | TCTAGAGTTT | CTCGAAGAGA | 2760 |

-continued

```
AACCATTAGT AGGAGAAGCG CTAGCTCGTG TGAAAAGAGC GGAGAAAAAA TGGAGAGACA    2820

AACGTGAAAA ATTGGAATGG GAAACAAATA TCGTTTATAA AGAGGCAAAA GAATCTGTAG    2880

ATGCTTTATT TGTAAACTCT CAATATGATC AATTACAAGC GGATACGAAT ATTGCCATGA    2940

TTCATGCGGC AGATAAACGT GTTCATAGCA TTCGAGAAGC TTGGCGTAAT CATGGTCATA    3000

CCTGTTTCCT GTGTGAAATT GTTATCCGCT CACAATTCCA CACAACATAC GAGCCGGAAG    3060

CATAAA                                                               3066
```

(2) INFORMATION FOR SEQ ID NO:4:

(i) SEQUENCE CHARACTERISTICS:
    (A) LENGTH: 969 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:4:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300
```

-continued

| | | | | | | | | | | | | | | |
|---|---|---|---|---|---|---|---|---|---|---|---|---|---|---|
| Ile | Tyr | Thr | Asp | Ala | His | Arg | Gly | Tyr | Tyr | Trp | Ser | Gly | His | Gln |
| 305 | | | | 310 | | | | 315 | | | | | | 320 |
| Ile | Met | Ala | Ser | Pro | Val | Gly | Phe | Ser | Gly | Pro | Glu | Phe | Thr | Phe | Pro |
| | | | 325 | | | | | 330 | | | | | 335 | |
| Leu | Tyr | Gly | Thr | Met | Gly | Asn | Ala | Ala | Pro | Gln | Gln | Arg | Ile | Val | Ala |
| | | | 340 | | | | 345 | | | | | 350 | | |
| Gln | Leu | Gly | Gln | Gly | Val | Tyr | Arg | Thr | Leu | Ser | Ser | Thr | Phe | Tyr | Arg |
| | | 355 | | | | | 360 | | | | | 365 | | |
| Arg | Pro | Phe | Asn | Ile | Gly | Ile | Asn | Asn | Gln | Gln | Leu | Ser | Val | Leu | Asp |
| | 370 | | | | 375 | | | | 380 | | | | | | |
| Gly | Thr | Glu | Phe | Ala | Tyr | Gly | Thr | Ser | Ser | Asn | Leu | Pro | Ser | Ala | Val |
| 385 | | | | | 390 | | | | 395 | | | | | 400 | |
| Tyr | Arg | Lys | Ser | Gly | Thr | Val | Asp | Ser | Leu | Asp | Glu | Ile | Pro | Pro | Gln |
| | | | | 405 | | | | | 410 | | | | 415 | | |
| Asn | Asn | Asn | Val | Pro | Pro | Arg | Gln | Gly | Phe | Ser | His | Arg | Leu | Ser | His |
| | | | 420 | | | | 425 | | | | | 430 | | | |
| Val | Ser | Met | Phe | Arg | Ser | Gly | Ser | Ser | Ser | Val | Ser | Ile | Ile | Arg |
| | | 435 | | | | | 440 | | | | 445 | | | |
| Ala | Pro | Met | Phe | Ser | Trp | Ile | His | Arg | Ser | Ala | Glu | Phe | Asn | Asn | Ile |
| | 450 | | | | | 455 | | | | | 460 | | | | |
| Ile | Ala | Ser | Asp | Ser | Ile | Thr | Gln | Ile | Pro | Ala | Val | Lys | Gly | Asn | Phe |
| 465 | | | | | 470 | | | | | 475 | | | | | 480 |
| Leu | Phe | Asn | Gly | Ser | Val | Ile | Ser | Gly | Pro | Gly | Phe | Thr | Gly | Gly | Asp |
| | | | | 485 | | | | | 490 | | | | | 495 | |
| Leu | Val | Arg | Leu | Asn | Ser | Ser | Gly | Asn | Asn | Ile | Gln | Asn | Arg | Gly | Tyr |
| | | | 500 | | | | | 505 | | | | | 510 | | |
| Ile | Glu | Val | Pro | Ile | His | Phe | Pro | Ser | Thr | Ser | Thr | Arg | Tyr | Arg | Val |
| | | 515 | | | | | 520 | | | | | 525 | | | |
| Arg | Val | Arg | Tyr | Ala | Ser | Val | Thr | Pro | Ile | His | Leu | Asn | Val | Asn | Trp |
| | 530 | | | | | 535 | | | | | 540 | | | | |
| Gly | Asn | Ser | Ser | Ile | Phe | Ser | Asn | Thr | Val | Pro | Ala | Thr | Ala | Thr | Ser |
| 545 | | | | | 550 | | | | | 555 | | | | | 560 |
| Leu | Asp | Asn | Leu | Gln | Ser | Ser | Asp | Phe | Gly | Tyr | Phe | Glu | Ser | Ala | Asn |
| | | | | 565 | | | | | 570 | | | | | 575 | |
| Ala | Phe | Thr | Ser | Ser | Leu | Gly | Asn | Ile | Val | Gly | Val | Arg | Asn | Phe | Ser |
| | | | 580 | | | | | 585 | | | | | 590 | | |
| Gly | Thr | Ala | Gly | Val | Ile | Ile | Asp | Arg | Phe | Glu | Phe | Ile | Pro | Val | Thr |
| | | 595 | | | | | 600 | | | | | 605 | | | |
| Ala | Thr | Leu | Glu | Ala | Glu | Tyr | Asn | Leu | Glu | Arg | Ala | Gln | Lys | Ala | Val |
| | 610 | | | | | 615 | | | | | 620 | | | | |
| Asn | Ala | Leu | Phe | Thr | Ser | Thr | Asn | Gln | Leu | Gly | Leu | Lys | Thr | Asn | Val |
| 625 | | | | | 630 | | | | | 635 | | | | | 640 |
| Thr | Asp | Tyr | His | Ile | Asp | Gln | Val | Ser | Asn | Leu | Val | Thr | Tyr | Leu | Ser |
| | | | | 645 | | | | | 650 | | | | | 655 | |
| Asp | Glu | Phe | Cys | Leu | Asp | Glu | Lys | Arg | Glu | Leu | Ser | Glu | Lys | Val | Lys |
| | | | 660 | | | | | 665 | | | | | 670 | | |
| His | Ala | Lys | Arg | Leu | Ser | Asp | Glu | Arg | Asn | Leu | Leu | Gln | Asp | Ser | Asn |
| | | 675 | | | | | 680 | | | | | 685 | | | |
| Phe | Lys | Asp | Ile | Asn | Arg | Gln | Pro | Glu | Arg | Gly | Trp | Gly | Gly | Ser | Thr |
| | 690 | | | | | 695 | | | | | 700 | | | | |
| Gly | Ile | Thr | Ile | Gln | Gly | Gly | Asp | Asp | Val | Phe | Lys | Glu | Asn | Tyr | Val |
| 705 | | | | | 710 | | | | | 715 | | | | | 720 |
| Thr | Leu | Ser | Gly | Thr | Phe | Asp | Glu | Cys | Tyr | Pro | Thr | Tyr | Leu | Tyr | Gln |
| | | | | 725 | | | | | 730 | | | | | 735 | |

5,424,409

-continued

| Lys | Ile | Asp | Glu | Ser | Lys | Leu | Lys | Ala | Phe | Thr | Arg | Tyr | Gln | Leu | Arg |
|     |     |     | 740 |     |     |     | 745 |     |     |     |     |     | 750 |     |     |

| Gly | Tyr | Ile | Glu | Asp | Ser | Gln | Asp | Leu | Glu | Ile | Tyr | Leu | Ile | Arg | Tyr |
|     |     |     | 755 |     |     |     | 760 |     |     |     |     |     | 765 |     |     |

| Asn | Ala | Lys | His | Glu | Thr | Val | Asn | Val | Pro | Gly | Thr | Gly | Ser | Leu | Trp |
|     |     |     | 770 |     |     |     | 775 |     |     |     |     |     | 780 |     |     |

| Pro | Leu | Ser | Ala | Gln | Ser | Pro | Ile | Gly | Lys | Cys | Gly | Glu | Pro | Asn | Arg |
| 785 |     |     |     |     | 790 |     |     |     |     | 795 |     |     |     |     | 800 |

| Cys | Ala | Pro | His | Leu | Glu | Trp | Asn | Pro | Asp | Leu | Asp | Cys | Ser | Cys | Arg |
|     |     |     |     | 805 |     |     |     |     | 810 |     |     |     |     | 815 |     |

| Asp | Gly | Glu | Lys | Cys | Ala | His | His | Ser | His | His | Phe | Ser | Leu | Asp | Ile |
|     |     |     | 820 |     |     |     |     | 825 |     |     |     |     |     | 830 |     |

| Asp | Val | Gly | Cys | Thr | Asp | Leu | Asn | Glu | Asp | Leu | Gly | Val | Trp | Val | Ile |
|     |     |     | 835 |     |     |     |     | 840 |     |     |     |     |     | 845 |     |

| Phe | Lys | Ile | Lys | Thr | Gln | Asp | Gly | His | Ala | Arg | Leu | Gly | Asn | Leu | Glu |
|     |     |     |     | 850 |     |     |     |     | 855 |     |     |     |     | 860 |     |

| Phe | Leu | Glu | Glu | Lys | Pro | Leu | Val | Gly | Glu | Ala | Leu | Ala | Arg | Val | Lys |
| 865 |     |     |     |     | 870 |     |     |     |     | 875 |     |     |     |     | 880 |

| Arg | Ala | Glu | Lys | Lys | Trp | Arg | Asp | Lys | Arg | Glu | Lys | Leu | Glu | Trp | Glu |
|     |     |     |     |     | 885 |     |     |     |     | 890 |     |     |     |     | 895 |

| Thr | Asn | Ile | Val | Tyr | Lys | Glu | Ala | Lys | Glu | Ser | Val | Asp | Ala | Leu | Phe |
|     |     |     |     | 900 |     |     |     |     | 905 |     |     |     |     | 910 |     |

| Val | Asn | Ser | Gln | Tyr | Asp | Gln | Leu | Gln | Ala | Asp | Thr | Asn | Ile | Ala | Met |
|     |     |     |     | 915 |     |     |     |     | 920 |     |     |     |     | 925 |     |

| Ile | His | Ala | Ala | Asp | Lys | Arg | Val | His | Ser | Ile | Arg | Glu | Ala | Trp | Arg |
|     |     |     |     | 930 |     |     |     |     | 935 |     |     |     |     | 940 |     |

| Asn | His | Gly | His | Ser | Cys | Phe | Leu | Cys | Glu | Ile | Val | Ile | Arg | Ser | Gln |
| 945 |     |     |     |     | 950 |     |     |     |     | 955 |     |     |     |     | 960 |

| Phe | His | Thr | Thr | Tyr | Glu | Pro | Glu | Ala |
|     |     |     |     | 965 |     |     |     |     |

( 2 ) INFORMATION FOR SEQ ID NO:5:

( i ) SEQUENCE CHARACTERISTICS:
        ( A ) LENGTH: 695 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| Met | Asp | Asn | Asn | Pro | Asn | Ile | Asn | Glu | Cys | Ile | Pro | Tyr | Asn | Cys | Leu |
| 1   |     |     |     | 5   |     |     |     |     | 10  |     |     |     |     | 15  |     |

| Ser | Asn | Pro | Glu | Val | Glu | Val | Leu | Gly | Gly | Glu | Arg | Ile | Glu | Thr | Gly |
|     |     |     | 20  |     |     |     | 25  |     |     |     |     |     | 30  |     |     |

| Tyr | Thr | Pro | Ile | Asp | Ile | Ser | Leu | Ser | Leu | Thr | Gln | Phe | Leu | Leu | Ser |
|     |     |     | 35  |     |     |     |     | 40  |     |     |     |     | 45  |     |     |

| Glu | Phe | Val | Pro | Gly | Ala | Gly | Phe | Val | Leu | Gly | Leu | Val | Asp | Ile | Ile |
|     |     |     | 50  |     |     |     |     | 55  |     |     |     |     | 60  |     |     |

| Trp | Gly | Ile | Phe | Gly | Pro | Ser | Gln | Trp | Asp | Ala | Phe | Leu | Val | Gln | Ile |
| 65  |     |     |     |     | 70  |     |     |     |     | 75  |     |     |     |     | 80  |

| Glu | Gln | Leu | Ile | Asn | Gln | Arg | Ile | Glu | Glu | Phe | Ala | Arg | Asn | Gln | Ala |
|     |     |     |     | 85  |     |     |     |     | 90  |     |     |     |     | 95  |     |

| Ile | Ser | Arg | Leu | Glu | Gly | Leu | Ser | Asn | Leu | Tyr | Gln | Ile | Tyr | Ala | Glu |
|     |     |     |     | 100 |     |     |     |     | 105 |     |     |     |     | 110 |     |

| Ser | Phe | Arg | Glu | Trp | Glu | Ala | Asp | Pro | Thr | Asn | Pro | Ala | Leu | Arg | Glu |
|     |     |     |     | 115 |     |     |     |     | 120 |     |     |     |     | 125 |     |

```
Glu  Met  Arg  Ile  Gln  Phe  Asn  Asp  Met  Asn  Ser  Ala  Leu  Thr  Thr  Ala
     130                      135                140

Ile  Pro  Leu  Phe  Ala  Val  Gln  Asn  Tyr  Gln  Val  Pro  Leu  Leu  Ser  Val
145                      150                     155                          160

Tyr  Val  Gln  Ala  Ala  Asn  Leu  His  Leu  Ser  Val  Leu  Arg  Asp  Val  Ser
               165                     170                          175

Val  Phe  Gly  Gln  Arg  Trp  Gly  Phe  Asp  Ala  Ala  Thr  Ile  Asn  Ser  Arg
               180                185                          190

Tyr  Asn  Asp  Leu  Thr  Arg  Leu  Ile  Gly  Asn  Tyr  Thr  Asp  His  Ala  Val
          195                      200                     205

Arg  Trp  Tyr  Asn  Thr  Gly  Leu  Glu  Arg  Val  Trp  Gly  Pro  Asp  Ser  Arg
     210                      215                     220

Asp  Trp  Ile  Arg  Tyr  Asn  Gln  Phe  Arg  Arg  Glu  Leu  Thr  Leu  Thr  Val
225                      230                     235                          240

Leu  Asp  Ile  Val  Ser  Leu  Phe  Pro  Asn  Tyr  Asp  Ser  Arg  Thr  Tyr  Pro
                    245                     250                     255

Ile  Arg  Thr  Val  Ser  Gln  Leu  Thr  Arg  Glu  Ile  Tyr  Thr  Asn  Pro  Val
               260                     265                     270

Leu  Glu  Asn  Phe  Asp  Gly  Ser  Phe  Arg  Gly  Ser  Ala  Gln  Gly  Ile  Glu
          275                     280                     285

Gly  Ser  Ile  Arg  Ser  Pro  His  Leu  Met  Asp  Ile  Leu  Asn  Ser  Ile  Thr
     290                     295                     300

Ile  Tyr  Thr  Asp  Ala  His  Arg  Gly  Glu  Tyr  Tyr  Trp  Ser  Gly  His  Gln
305                     310                     315                          320

Ile  Met  Ala  Ser  Pro  Val  Gly  Phe  Ser  Gly  Pro  Glu  Phe  Thr  Phe  Pro
               325                     330                     335

Leu  Tyr  Gly  Thr  Met  Gly  Asn  Ala  Ala  Pro  Gln  Gln  Arg  Ile  Val  Ala
               340                     345                     350

Gln  Leu  Gly  Gln  Gly  Val  Tyr  Arg  Thr  Leu  Ser  Ser  Thr  Leu  Tyr  Arg
          355                     360                     365

Arg  Pro  Phe  Asn  Ile  Gly  Ile  Asn  Asn  Gln  Gln  Leu  Ser  Val  Leu  Asp
     370                     375                     380

Gly  Thr  Glu  Phe  Ala  Tyr  Gly  Thr  Ser  Ser  Asn  Leu  Pro  Ser  Ala  Val
385                     390                     395                          400

Tyr  Arg  Lys  Ser  Gly  Thr  Val  Asp  Ser  Leu  Asp  Glu  Ile  Pro  Pro  Gln
                    405                     410                     415

Asn  Asn  Asn  Val  Pro  Pro  Arg  Gln  Gly  Phe  Ser  His  Arg  Leu  Ser  His
               420                     425                     430

Val  Ser  Met  Phe  Arg  Ser  Gly  Phe  Ser  Asn  Ser  Ser  Val  Ser  Ile  Ile
          435                     440                     445

Arg  Ala  Pro  Met  Phe  Ser  Trp  Ile  His  Arg  Ser  Ala  Glu  Phe  Asn  Asn
450                     455                     460

Ile  Ile  Pro  Ser  Ser  Gln  Ile  Thr  Gln  Ile  Pro  Leu  Thr  Lys  Ser  Thr
465                     470                     475                          480

Asn  Leu  Gly  Ser  Gly  Thr  Ser  Val  Val  Lys  Gly  Pro  Gly  Phe  Thr  Gly
                    485                     490                     495

Gly  Asp  Ile  Leu  Arg  Arg  Thr  Ser  Pro  Gly  Gln  Ile  Ser  Thr  Leu  Arg
               500                     505                     510

Val  Asn  Ile  Thr  Ala  Pro  Leu  Ser  Gln  Arg  Tyr  Arg  Val  Arg  Ile  Arg
          515                     520                     525

Tyr  Ala  Ser  Thr  Thr  Asn  Leu  Gln  Phe  His  Thr  Ser  Ile  Asp  Gly  Arg
          530                     535                     540

Pro  Ile  Asn  Gln  Gly  Asn  Phe  Ser  Ala  Thr  Met  Ser  Ser  Gly  Ser  Asn
545                     550                     555                          560

Leu  Gln  Ser  Gly  Ser  Phe  Arg  Thr  Val  Gly  Phe  Thr  Thr  Pro  Phe  Asn
```

|     |     |     |     | 565 |     |     |     |     | 570 |     |     |     |     | 575 |     |
| --- | --- | --- | --- | --- | --- | --- | --- | --- | --- | --- | --- | --- | --- | --- | --- |
| Phe | Ser | Asn | Gly | Ser | Ser | Val | Phe | Thr | Leu | Ser | Ala | His | Val | Phe | Asn |
|     |     |     | 580 |     |     |     |     | 585 |     |     |     | 590 |     |     |     |
| Ser | Gly | Asn | Glu | Val | Tyr | Ile | Asp | Arg | Ile | Glu | Phe | Val | Pro | Ala | Glu |
|     |     | 595 |     |     |     | 600 |     |     |     |     | 605 |     |     |     |     |
| Val | Thr | Phe | Glu | Ala | Glu | Tyr | Asp | Leu | Glu | Arg | Ala | Gln | Lys | Ala | Val |
|     | 610 |     |     |     | 615 |     |     |     |     | 620 |     |     |     |     |     |
| Asn | Glu | Leu | Phe | Thr | Ser | Ser | Asn | Gln | Ile | Gly | Leu | Lys | Thr | Asp | Val |
| 625 |     |     |     | 630 |     |     |     |     | 635 |     |     |     |     |     | 640 |
| Thr | Asp | Tyr | His | Ile | Asp | Gln | Val | Ser | Asn | Leu | Val | Glu | Cys | Leu | Ser |
|     |     |     | 645 |     |     |     |     | 650 |     |     |     |     | 655 |     |     |
| Asp | Glu | Phe | Cys | Leu | Asp | Glu | Lys | Lys | Glu | Leu | Ser | Glu | Lys | Val | Lys |
|     |     | 660 |     |     |     |     | 665 |     |     |     |     | 670 |     |     |     |
| His | Ala | Asn | Asp | Leu | Val | Met | Ser | Gly | Ile | Tyr | Phe | Lys | Ile | Gln | Thr |
|     | 675 |     |     |     |     | 680 |     |     |     |     | 685 |     |     |     |     |
| Leu | Glu | Gly | Ser | Ile | Asp | Asn |     |     |     |     |     |     |     |     |     |
| 690 |     |     |     |     | 695 |     |     |     |     |     |     |     |     |     |     |

( 2 ) INFORMATION FOR SEQ ID NO:6:

( i ) SEQUENCE CHARACTERISTICS:
( A ) LENGTH: 969 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Asp | Asn | Asn | Pro | Asn | Ile | Asn | Glu | Cys | Ile | Pro | Tyr | Asn | Cys | Leu |
| 1   |     |     |     | 5   |     |     |     |     | 10  |     |     |     |     | 15  |     |
| Ser | Asn | Pro | Glu | Val | Glu | Val | Leu | Gly | Gly | Glu | Arg | Ile | Glu | Thr | Gly |
|     |     |     | 20  |     |     |     |     | 25  |     |     |     |     | 30  |     |     |
| Tyr | Thr | Pro | Ile | Asp | Ile | Ser | Leu | Ser | Leu | Thr | Gln | Phe | Leu | Leu | Ser |
|     |     | 35  |     |     |     |     | 40  |     |     |     |     | 45  |     |     |     |
| Glu | Phe | Val | Pro | Gly | Ala | Gly | Phe | Val | Leu | Gly | Leu | Val | Asp | Ile | Ile |
|     | 50  |     |     |     |     | 55  |     |     |     |     | 60  |     |     |     |     |
| Trp | Gly | Ile | Phe | Gly | Pro | Ser | Gln | Trp | Asp | Ala | Phe | Leu | Val | Gln | Ile |
| 65  |     |     |     |     | 70  |     |     |     |     | 75  |     |     |     |     | 80  |
| Glu | Gln | Leu | Ile | Asn | Gln | Arg | Ile | Glu | Glu | Phe | Ala | Arg | Asn | Gln | Ala |
|     |     |     |     | 85  |     |     |     |     | 90  |     |     |     |     | 95  |     |
| Ile | Ser | Arg | Leu | Glu | Gly | Leu | Ser | Asn | Leu | Tyr | Gln | Ile | Tyr | Ala | Glu |
|     |     |     | 100 |     |     |     |     | 105 |     |     |     |     | 110 |     |     |
| Ser | Phe | Arg | Glu | Trp | Glu | Ala | Asp | Pro | Thr | Asn | Pro | Ala | Leu | Arg | Glu |
|     |     | 115 |     |     |     |     | 120 |     |     |     |     | 125 |     |     |     |
| Glu | Met | Arg | Ile | Gln | Phe | Asn | Asp | Met | Asn | Ser | Ala | Leu | Thr | Thr | Ala |
|     | 130 |     |     |     |     | 135 |     |     |     |     | 140 |     |     |     |     |
| Ile | Pro | Leu | Phe | Ala | Val | Gln | Asn | Tyr | Gln | Val | Pro | Leu | Leu | Ser | Val |
| 145 |     |     |     |     | 150 |     |     |     |     | 155 |     |     |     |     | 160 |
| Tyr | Val | Gln | Ala | Ala | Asn | Leu | His | Leu | Ser | Val | Leu | Arg | Asp | Val | Ser |
|     |     |     |     | 165 |     |     |     |     | 170 |     |     |     |     | 175 |     |
| Val | Phe | Gly | Gln | Arg | Trp | Gly | Phe | Asp | Ala | Ala | Thr | Ile | Asn | Ser | Arg |
|     |     |     | 180 |     |     |     |     | 185 |     |     |     |     | 190 |     |     |
| Tyr | Asn | Asp | Leu | Thr | Arg | Leu | Ile | Gly | Asn | Tyr | Thr | Asp | His | Ala | Val |
|     |     | 195 |     |     |     |     | 200 |     |     |     |     | 205 |     |     |     |
| Arg | Trp | Tyr | Asn | Thr | Gly | Leu | Glu | Arg | Val | Trp | Gly | Pro | Asp | Ser | Arg |
|     | 210 |     |     |     |     | 215 |     |     |     |     | 220 |     |     |     |     |
| Asp | Trp | Ile | Arg | Tyr | Asn | Gln | Phe | Arg | Arg | Glu | Leu | Thr | Leu | Thr | Val |

-continued

```
        225                     230                      235                     240
    Leu  Asp  Ile  Val  Ser  Leu  Phe  Pro  Asn  Tyr  Asp  Ser  Arg  Thr  Tyr  Pro
                        245                     250                     255
    Ile  Arg  Thr  Val  Ser  Gln  Leu  Thr  Arg  Glu  Ile  Tyr  Thr  Asn  Pro  Val
                        260                     265                     270
    Leu  Glu  Asn  Phe  Asp  Gly  Ser  Phe  Arg  Gly  Ser  Ala  Gln  Gly  Ile  Glu
                        275                     280                     285
    Gly  Ser  Ile  Arg  Ser  Pro  His  Leu  Met  Asp  Ile  Leu  Asn  Ser  Ile  Thr
                        290                     295                     300
    Ile  Tyr  Thr  Asp  Ala  His  Arg  Gly  Glu  Tyr  Tyr  Trp  Ser  Gly  His  Gln
    305                     310                     315                         320
    Ile  Met  Ala  Ser  Pro  Val  Gly  Phe  Ser  Gly  Pro  Glu  Phe  Thr  Phe  Pro
                        325                     330                     335
    Leu  Tyr  Gly  Thr  Met  Gly  Asn  Ala  Ala  Pro  Gln  Gln  Arg  Ile  Val  Ala
                        340                     345                     350
    Gln  Leu  Gly  Gln  Gly  Val  Tyr  Arg  Thr  Leu  Ser  Ser  Thr  Leu  Tyr  Arg
                        355                     360                     365
    Arg  Pro  Phe  Asn  Ile  Gly  Ile  Asn  Asn  Gln  Gln  Leu  Ser  Val  Leu  Asp
         370                     375                     380
    Gly  Thr  Glu  Phe  Ala  Tyr  Gly  Thr  Ser  Ser  Asn  Leu  Pro  Ser  Ala  Val
    385                     390                     395                         400
    Tyr  Arg  Lys  Ser  Gly  Thr  Val  Asp  Ser  Leu  Asp  Glu  Ile  Pro  Pro  Gln
                        405                     410                     415
    Asn  Asn  Asn  Val  Pro  Pro  Arg  Gln  Gly  Phe  Ser  His  Arg  Leu  Ser  His
                        420                     425                     430
    Val  Ser  Met  Phe  Arg  Ser  Gly  Phe  Ser  Asn  Ser  Ser  Val  Ser  Ile  Ile
                        435                     440                     445
    Arg  Ala  Pro  Met  Phe  Ser  Trp  Ile  His  Arg  Ser  Ala  Glu  Phe  Asn  Asn
    450                     455                     460
    Ile  Ile  Pro  Ser  Ser  Gln  Ile  Thr  Gln  Ile  Pro  Leu  Thr  Lys  Ser  Thr
    465                     470                     475                         480
    Asn  Leu  Gly  Ser  Gly  Thr  Ser  Val  Val  Lys  Gly  Pro  Gly  Phe  Thr  Gly
                        485                     490                     495
    Gly  Asp  Ile  Leu  Arg  Arg  Thr  Ser  Pro  Gly  Gln  Ile  Ser  Thr  Leu  Arg
                        500                     505                     510
    Val  Asn  Ile  Thr  Ala  Pro  Leu  Ser  Gln  Arg  Tyr  Arg  Val  Arg  Ile  Arg
                        515                     520                     525
    Tyr  Ala  Ser  Thr  Thr  Asn  Leu  Gln  Phe  His  Thr  Ser  Ile  Asp  Gly  Arg
                        530                     535                     540
    Pro  Ile  Asn  Gln  Gly  Asn  Phe  Ser  Ala  Thr  Met  Ser  Ser  Gly  Ser  Asn
    545                     550                     555                         560
    Leu  Gln  Ser  Gly  Ser  Phe  Arg  Thr  Val  Gly  Phe  Thr  Thr  Pro  Phe  Asn
                        565                     570                     575
    Phe  Ser  Asn  Gly  Ser  Ser  Val  Phe  Thr  Leu  Ser  Ala  His  Val  Phe  Asn
                        580                     585                     590
    Ser  Gly  Asn  Glu  Val  Tyr  Ile  Asp  Arg  Ile  Glu  Phe  Val  Pro  Ala  Glu
                        595                     600                     605
    Val  Thr  Phe  Glu  Ala  Glu  Tyr  Asp  Leu  Glu  Arg  Ala  Gln  Lys  Ala  Val
         610                     615                     620
    Asn  Glu  Leu  Phe  Thr  Ser  Ser  Asn  Gln  Ile  Gly  Leu  Lys  Thr  Asp  Val
    625                     630                     635                         640
    Thr  Asp  Tyr  His  Ile  Asp  Gln  Val  Ser  Asn  Leu  Val  Glu  Cys  Leu  Ser
                        645                     650                     655
    Asp  Glu  Phe  Cys  Leu  Asp  Glu  Lys  Gln  Glu  Leu  Ser  Glu  Lys  Val  Lys
                        660                     665                     670
```

```
His Ala Lys Arg Leu Ser Asp Glu Arg Asn Leu Leu Gln Asp Pro Asn
        675                 680                 685
Phe Arg Gly Ile Asn Arg Gln Leu Asp Arg Gly Trp Arg Gly Ser Thr
    690                 695                 700
Asp Ile Thr Ile Gln Gly Gly Asp Asp Val Phe Lys Glu Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
            740                 745                 750
Gly Tyr Ile Glu Asp Ser Gln Asp Leu Glu Ile Tyr Leu Ile Arg Tyr
        755                 760                 765
Asn Ala Lys His Glu Thr Val Asn Val Pro Gly Thr Gly Ser Leu Trp
    770                 775                 780
Pro Leu Ser Ala Gln Ser Pro Ile Gly Lys Cys Gly Glu Pro Asn Arg
785                 790                 795                 800
Cys Ala Pro His Leu Glu Trp Asn Pro Asp Leu Asp Cys Ser Cys Arg
                805                 810                 815
Asp Gly Glu Lys Cys Ala His His Ser His His Phe Ser Leu Asp Ile
            820                 825                 830
Asp Val Gly Cys Thr Asp Leu Asn Glu Asp Leu Gly Val Trp Val Ile
        835                 840                 845
Phe Lys Ile Lys Thr Gln Asp Gly His Ala Arg Leu Gly Asn Leu Glu
850                 855                 860
Phe Leu Glu Glu Lys Pro Leu Val Gly Glu Ala Leu Ala Arg Val Lys
865                 870                 875                 880
Arg Ala Glu Lys Lys Trp Arg Asp Lys Arg Glu Lys Leu Glu Trp Glu
                885                 890                 895
Thr Asn Ile Val Tyr Lys Glu Ala Lys Glu Ser Val Asp Ala Leu Phe
            900                 905                 910
Val Asn Ser Gln Tyr Asp Gln Leu Gln Ala Asp Thr Asn Ile Ala Met
        915                 920                 925
Ile His Ala Ala Asp Lys Arg Val His Ser Ile Arg Glu Ala Trp Arg
    930                 935                 940
Asn His Gly His Thr Cys Phe Leu Cys Glu Ile Val Ile Arg Ser Gln
945                 950                 955                 960
Phe His Thr Thr Tyr Glu Pro Glu Ala
                965
```

* * * * *